(12) United States Patent
Forsell

(10) Patent No.: US 9,700,336 B2
(45) Date of Patent: Jul. 11, 2017

(54) SURGICAL INSTRUMENT

(76) Inventor: Peter Forsell, Bouveret (CH)

(*) Notice: Subject to any disclaimer, the term of this patent is extended or adjusted under 35 U.S.C. 154(b) by 642 days.

(21) Appl. No.: 13/384,077

(22) PCT Filed: Jul. 19, 2010

(86) PCT No.: PCT/SE2010/050861
§ 371 (c)(1),
(2), (4) Date: Jan. 13, 2012

(87) PCT Pub. No.: WO2011/008167
PCT Pub. Date: Jan. 20, 2011

(65) Prior Publication Data
US 2012/0116415 A1    May 10, 2012

Related U.S. Application Data

(60) Provisional application No. 61/213,814, filed on Jul. 17, 2009.

(30) Foreign Application Priority Data

Jul. 17, 2009 (SE) ........................................ 0901011

(51) Int. Cl.
| A61B 17/42 | (2006.01) |
| A61B 17/29 | (2006.01) |
| A61F 2/00 | (2006.01) |
| A61F 2/30 | (2006.01) |

(52) U.S. Cl.
CPC ............ *A61B 17/29* (2013.01); *A61F 2/0036* (2013.01); *A61B 2017/2905* (2013.01); *A61B 2017/2908* (2013.01); *A61B 2017/2927* (2013.01); *A61F 2002/30668* (2013.01); *A61F 2250/0001* (2013.01)

(58) Field of Classification Search
CPC ............ A61B 17/29; A61B 2017/2905; A61B 2017/2908; A61B 2017/2927
USPC ................................ 606/119, 170, 174, 205
See application file for complete search history.

(56) References Cited

U.S. PATENT DOCUMENTS

| 5,275,608 A * | 1/1994 | Forman et al. ............... 606/170 |
| 5,618,294 A | 4/1997 | Aust et al. |
| 2001/0056282 A1 | 12/2001 | Sonnenschein et al. |
| 2007/0156012 A1 | 7/2007 | Tracey et al. |
| 2008/0004487 A1 | 1/2008 | Haverfield |

OTHER PUBLICATIONS

International Search Report for PCT/SE2010/050861, mailed Nov. 3, 2010.

* cited by examiner

*Primary Examiner* — Ashley Fishback

(57) ABSTRACT

There is provided a surgical instrument that simplifies surgery for implantation surgery for treating anal incontinence in women. The disclosed surgical instrument is intended to be inserted through an incision in the vagina and is used for dissecting tissue as well as positioning the implant. The instrument comprises a main part of the instrument, an elongated member with a flexible tip and can change conformation from a straight conformation to a loop conformation that can reach around a portion of the rectum.

20 Claims, 21 Drawing Sheets

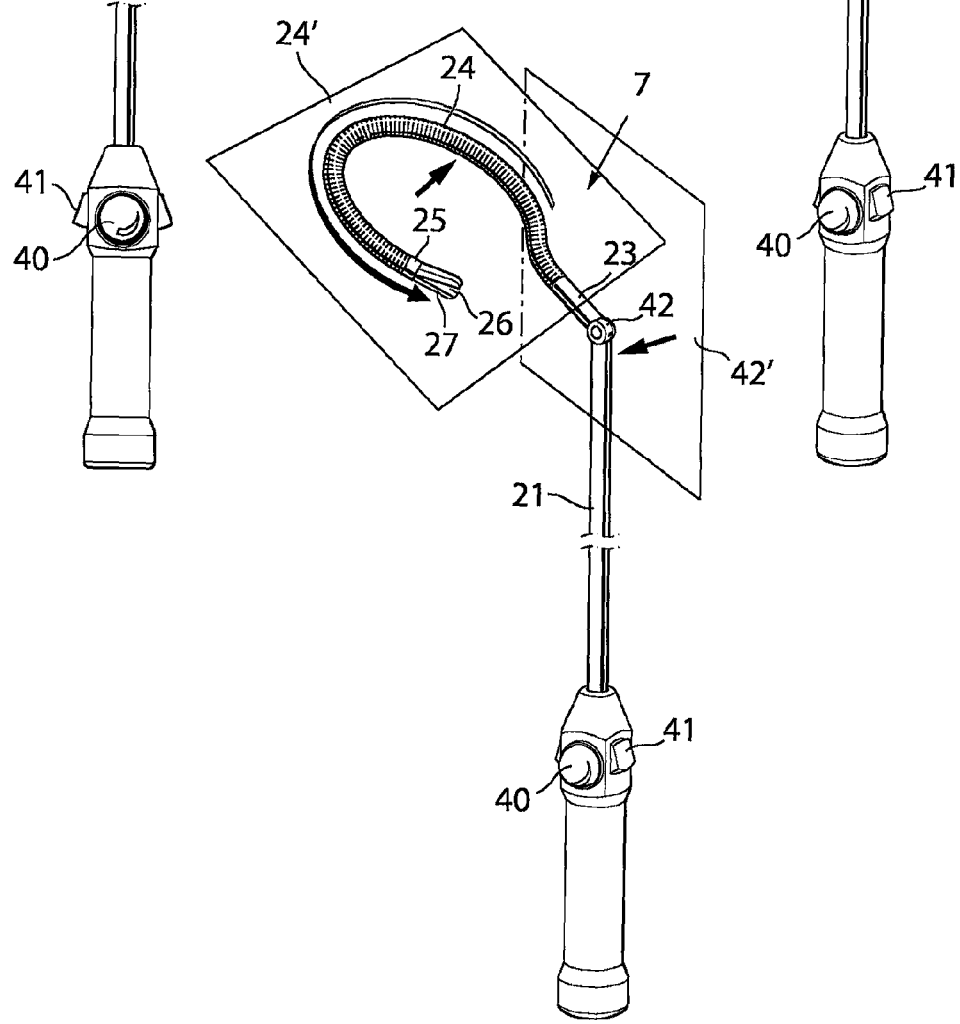

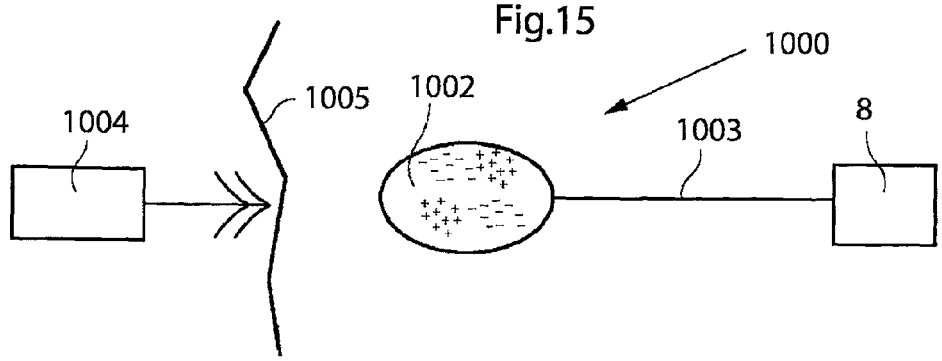
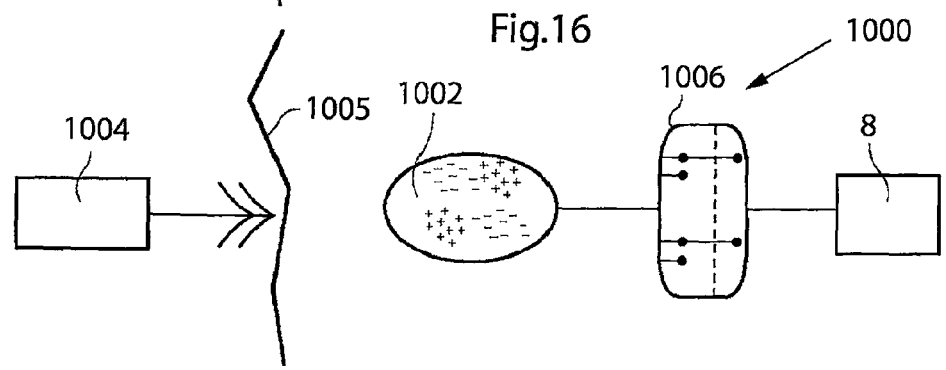
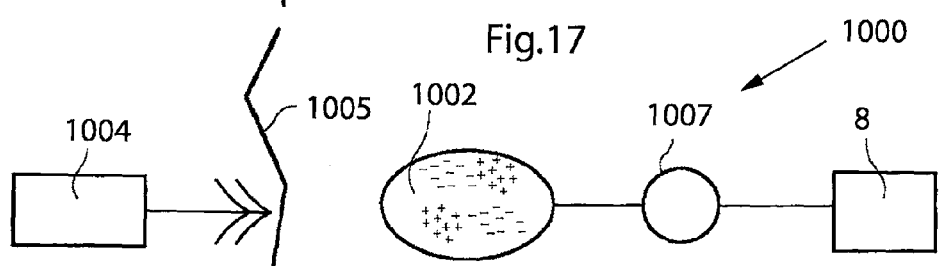
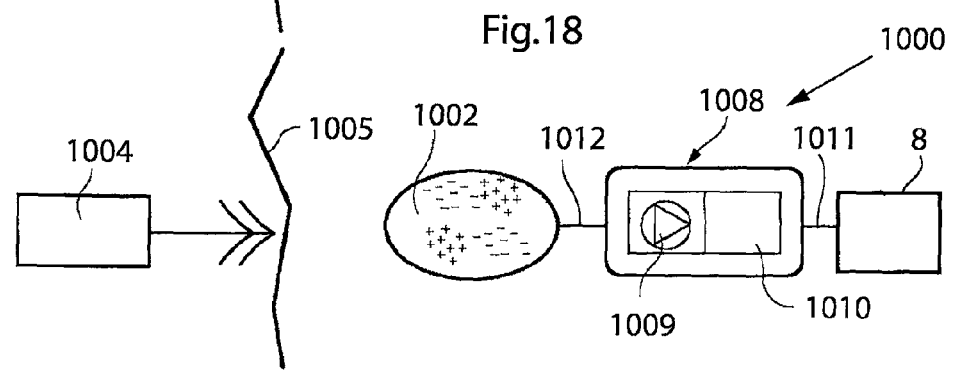

SURGICAL INSTRUMENT

This application is the U.S. national phase of International Application No. PCT/SE2010/050861, filed 19 Jul. 2010, which designated the U.S. and claims the benefit of U.S. Provisional Application No.: 61/213,814 filed 17 Jul. 2009 and which claims priority to Swedish Application No.: 0901011-7, filed 17 Jul. 2009 the entire contents of each of which are hereby incorporated by reference.

FIELD OF THE INVENTION

The present invention relates to surgical instrument for obtaining better access to body cavities and simplify implantation of medical devices, in particular restriction devices operable to restrict and release body canals.

BACKGROUND

Anal and urinary incontinence is a widespread problem that severely lowers the quality of life of those affected. Many different solutions to this problem have been tried. Several kinds of sphincter plastic surgery are for instance used today to remedy anal incontinence. Long term success rates are, however, poor: more than 50% of patients become incontinent again within ten years after surgery (Halverson and Hull Dis Colon Rectum 2002 March; 45 (3):345-8, and Gutierrez et al Dis Colon Rectum 2004 May; 47(5):727-31)

There is also the possibility to implant an artificial anal sphincter. A manually operated sphincter for men with a hydraulic sphincter system connected to a reservoir placed in the scrotum, is for instance known (U.S. Pat. No. 4,222, 377). U.S. Pat. No. 5,593,443 discloses hydraulic anal sphincter under both reflex and voluntary control. One disadvantage of this system is that hard fibrosis formed around the reservoir over time may cause malfunction of pumping components. Thus, the formed fibrosis will sooner or later become a hard fibrotic layer which may make it difficult to pump the reservoir. Furthermore, it is a rather complicated task to mechanically manually pump the reservoir when defecation is needed.

Another important complication with previous methods is the infection risk during surgery. It is not unusual with infection rates of 20%-50% in artificial bowel sphincter surgery (Melenhorst et al, Int J Colorectal Dis 2008 January; 23(1)107-11). Infections at this site cause wounds that are very painful and that takes several weeks to heal.

In the context of treating urinary incontinence in women, it is previously known that the urethra can be accessed through the vagina in order to for instance 1) place a staple into the pelvic bone that lifts and supports the bladder and the urethra (WO 92/16152)2), inserting a sling that supports the urethra (U.S. Pat. No. 6,641,524), and 3) inserting a shaft that guides a sling that is anchored and supports the bladder (US 2008/0125621 A1).

U.S. Pat. No. 6,911,003 disclose a rigid surgical instrument for inserting a sling for the treatment of urinary incontinence. This instrument is helix-shaped and is intended to be inserted through an incision in the pelvis.

US patent application 2008/0004487 discloses the use of an instrument disclosed in U.S. Pat. No. 6,911,003 for treating anal incontinence in women. The disclosed method suggests the insertion of the instrument trough an incision in the pelvis.

Restriction devices for the treatment of anal insentience that engage the rectum and stop the movement of faces by reducing the cross-section of the lumen of the rectum are known. Examples include to U.S. Pat. No. 7,367,938 and EP 1 255 511.

SUMMARY OF THE INVENTION

It is general object of the invention to provide a surgical instrument with improved operability in body cavities of the patient, such as the abdominal cavity. The instrument may be used for several surgical procedures preferable laparoscopic procedures. The instrument may for example be used to take any part of the body or any part of implanted material around a body part or around any other part of implanted material.

It is another specific object of the present invention to obviate at disadvantages found in the prior surgical methods and provide and a surgical instrument that is operable in abdominal cavity through an incision the vaginal wall for treating a female patient, while providing a methodology wherein the surgical instrument operates on a device to be implanted for treating anal incontinence or urine incontinence by controlling the faecal and urinary passageways.

In first general aspect the invention relates to a surgical instrument with improved operability when implanting a medical device in a body cavity. The instrument generally has an elongated main part attached to an elongated member, wherein an angle (A) between the extension of the main part of the instrument (21) and the elongated member is between 0 and less than 180 degrees. The elongated member further comprises a flexible tip that exhibits a conformation which is reversibly changeable from an essentially straight conformation to a loop conformation, where the flexible tip comprises a dissector, and where the flexible tip comprises an attachment structure adapted to attach to an implantable restriction device. The angle (A) between the main part of the instrument and the elongated member is adjustable; preferably, the angle A is adjustable independently from the change of conformation of the flexible tip. It is also preferred that the elongated member can be turned around its own axis so that the plane of the loop is continuously adjustable. For the purpose of adjusting the angle (A) independently of the conformation of the flexible tip, the surgical device can be provided with an adjustable joint for adjusting the angle (A) between the main part of the instrument and the elongated member. In addition, the surgical instrument can comprise an additional adjustable joint located on the elongated member for adjusting the angle B between two park of the elongated member, preferable independently of the conformation of the flexible tip.

The disclosed surgical instrument is particularly useful to be inserted from an incision in the vagina and then change its shape so that it extends around the rectum or colon, or around the urethra.

One embodiment outlines a surgical instrument for accessing an opening in the vaginal wall of a patient comprising A surgical instrument, the instrument comprising:
an elongated main part (21),
an elongated member (23) attached to the elongated main part by means of a first joint (42) having a pivotal axis, wherein a first angle (A) between the main part of the instrument and the elongated member is between 0 and 180 degrees, and wherein a first plane (42') extends perpendicularly to the pivotal axis, so that the elongated main part and the elongated member lies in the first plane,
a flexible tip (24) provided on the elongated member and exhibiting a conformation which is reversibly changeable from an essentially straight conformation to a loop or hook conformation, wherein the flexible tip, when in the loop or hook conformation, defines an opening with an axial hole going there through, and wherein a second plane (24') extends perpendicularly to the axial hole through said loop or hook, so that the flexible tip, in its loop or hook conformation, lies in the second plane, wherein the flexible tip comprises a dissector and an attachment structure adapted to attach to an implantable medical device, the first angle (A) is adjustable independently from the change of conformation of the flexible tip, and the orientation of the first plane is different from the orientation of the second plane.

In one embodiment the surgical instrument have the first plane different from the second plane of between 5 and less than 90 degrees or different from the second plane between 50 and 70 degrees or different from the second plane between 30 and 120 degrees.

In one embodiment, the bending of the flexible tip is controlled by a means selected from the group consisting of a mechanical manipulation, an electric control device and a hydraulic fluid system.

In a specific aspect, demonstrating a surgical method to treat anal incontinence, the invention provides a methodology comprising the steps of a) accessing trough an opening in the vaginal wall of the patient, at least one organ selected from group consisting of: the colon, the rectum and the anal channel and sphincter, b) dissecting in the patient at least one organ selected from the group consisting of the colon, the rectum, anus and the anal sphincter, c) implanting at least one powered restriction device in a position that enables it to at least partially restrict the movement of faeces through the rectum and/or anus, wherein said restriction device is used to decrease the cross sectional area of the faecal passageway in order to at least decrease the movement of faces through said passageway.

In another exemplifying aspect, the invention provides an implantable restriction device for the treatment of anal incontinence in women that engages the colon or rectum by forming a loop around the colon or rectum characterised in that said device can adapt a straight conformation during implantation of the device and a loop conformation when the device is implanted and engaging the colon or rectum, and where said straight conformation has a) surface with low friction relative to body tissue, b) has a shape that is streamlined with respect to movement in the direction of the main axis of the device in its straight conformation.

The disclosed restriction device preferably has a smooth surface without protruding park that makes it adapted to be dragged around behind the rectum by the surgical instrument without snagging or getting stuck.

When performing a surgical treatment of anal incontinence, the restriction device is intended to work together with the surgical instrument as follows. The restriction device can adopt two conformations: a straight conformation and a loop conformation. The straight conformation is used during surgical implantation. The disclosed surgical instrument can reach around behind the rectum, connect to the restriction device in its straight conformation and drag it into place behind the rectum. The restriction device can then be closed to form a loop around the rectum or colon.

One advantage with the disclosed invention is that the risk of infection is reduced compared to surgery accessing the rectum or colon from the outside. This is because the acid environment of the vagina makes it very hostile to pathogens. By accessing the colon or rectum though an incision in the vagina, patient trauma and discomfort can be kept to a minimum. This will shorten recovery time.

Another advantage of the invention is that it does not involve complicated surgery.

Another advantage is that a restriction device can be placed low, near the anus. This has the advantage that the faeces will be stored in the natural ampulla also after surgery. Placing the restriction device high causes faeces to be stored too high in the colon, which is disadvantageous. Placing the device in closer to the anal sphincter muscle will enable placement in a region below the abdominal cavity reducing risk if the restriction device would as a complication penetrate the intestine.

Surgical Instrument

In a first aspect the invention provides a surgical instrument comprising an elongated main part of the instrument attached to an elongated member. The angle (A) between the extension of the main part of the instrument and the elongated member is between 0 and less than 180 degrees. Further, the elongated member comprises a flexible tip, exhibiting a conformation which is reversibly changeable from an essentially straight conformation to a loop conformation, where the plane of the loop is different from the plane shared by the main part of the instrument and the elongated member. Also, the flexible tip comprises a dissector, and the flexible tip comprises an attachment structure adapted to attach to an implantable restriction device.

In one embodiment the angle (A) between the main part of the instrument and the elongated member is adjustable.

In one embodiment the angle A is adjustable independently from the change of conformation of the flexible tip. Preferably, the surgical instrument according comprises an adjustable joint for adjusting the angle (A) between the main part of the instrument and the elongated member, independently of the conformation of the flexible tip. According to a special alternative the surgical instrument according comprises an additional adjustable joint located on the elongated member for adjusting the angle between two parts of the elongated member. Preferably, the additional joint is adjustable independently of how the first joint is adjusted and the conformation of the flexible tip. By the additional joint the elongated member will be provided with two park which can be adjusted so that an angle (B) is formed between the parts. The introduction of an additional joint serves to facilitate bending the elongated member around a body lumen when introducing the instrument with the attached restriction device to implanted. Angles (A) and (B) can preferably retain the same angular intervals, but are preferably, adjustable independently of each other in order to obtain optimal flexibility of the instrument. The additional joint increases the flexibility when operating the surgical instrument. Both Angle A and B and thereby joint 42 and may in a special embodiment be rotated around ifs own axis before it is angled thus allowing 360° or less turn-around. The same turnaround may be supplied for the flexible tip.

In this embodiment of the surgical instrument a third plane is defined as the plane created by the in angle B bent instrument shared by the two parts of the elongated member, filling out the distances between the two elongated parts at the angle B wherein said plane Bis at least different from; said first plane and said second plane. In other words, a third plane is defined as extending perpendicularly to the pivotal axis of the additional joint, so that the two parts of the elongated member lie in this third plane. The orientation of this third plane is so that it is different from the orientation of the first plane or the second plane, or preferably both the first plane and the second plane, thereby increasing the flexibility of the instrument.

In one embodiment the elongated member can be turned around its own axis so that the plane of the loop is continuously adjustable.

In one embodiment the attachment structure comprises a quick coupling.

In one embodiment the attachment structure comprises a pincer.

In one embodiment the instrument comprises a viewing scope.

In one embodiment the dissector is a tissue dissector.

In one embodiment the instrument comprises a camera. This camera is adapted to assist moving the instrument into an opening in the vaginal wall of a patient.

In one embodiment the angle A is between 20 and 170 degrees. In one embodiment the angle A is between 60 and 150 degrees. In one embodiment the angle A is between 60 and 140 degrees. In one embodiment the angle A is between 90 and 180 degrees. In one embodiment the angle A is between 90 and 170 degrees. In one embodiment the angle A is between 90 and 160 degrees. In one embodiment the angle A is between 90 and 150 degrees. In one embodiment the angle A is between 90 and 140 degrees. In one embodiment the angle A is between 100 and 180 degrees. In one embodiment the angle A is between 100 and 170 degrees. In one embodiment the angle A is between 100 and 160 degrees. In one embodiment the angle A is between 100 and 150 degrees. In one embodiment the angle A is between 100 and 140 degrees. In one embodiment the angle A is variable within said intervals. Angle B can retain the same angular intervals, but is preferably, adjustable independently of angle A, with the additional joint.

In one embodiment the main part of the instrument is extendable. In one embodiment the main part of the instrument is continuously extendable.

In one embodiment the change of conformation of the loop is achieved by wires that run inside the flexible tip.

In one embodiment the surgical instrument further comprises a control unit that can independently control any parameter from the group selected from the change of conformation of the flexible tip, the attachment structure, the angle A, turning of the two park of the elongated member around their own axis independently from each other, turning of the elongated member around its own axis, and extension of the main part of the instrument.

In one embodiment the control unit is integrated into the handle of the instrument. The angles (A) and (B) may be adjustable independently of each other and independently the conformation of the flexible tip.

The handle may include an adjustment device integrated in the handle, wherein said adjustment device is capable of adjusting any of the joints and the flexible separately or in optional combinations.

The surgical instrument may include at least one position sensor, located on one or more of flexible tip and parts of the elongated member, wherein said at least one sensor is capable sending a signal to the control unit representing the location of at least one of the flexible tip and the parts of the elongated member.

The adjustment device may adjust the adjustable joint for adjusting the angle (A) between the main part of the instrument and the elongated member as well as the additional adjustable joint located on the elongated member for adjusting the angle (B) between two park of the elongated member.

At least one of the angles A and B may be adjustable dependently from the change of conformation of the flexible tip. The respective movement of angle A and B may be related to each other especially the rotation around the axis o the elongated member.

Although, the surgical instrument as described will be exemplified in methods for treating anal incontinence in female patients, it should be regarded as widely applicable when implanting a medical device in a body cavity. In particular, the presently invented surgical instrument is useful for implanting restriction devices operable to restrict and release body canals.

General Method for Treatment and Surgery

In an exemplifying aspect of the invention, there is provided a method for surgery to be performed on a female patient suffering from anal incontinence, whereby the faecal passageway is accessed through an incision in the vaginal wall of the patient. In addition there is provided a surgical instrument for carrying out the procedure and a restriction device adapted to work in concert with the surgical instrument.

There is provided a method for treating a female anal incontinent patient, the method comprising the steps of: a) accessing trough an opening in the vaginal wall of the patient, at least one organ selected from group consisting of the colon, the rectum and the anal sphincter, b) dissecting in the patient at least one organ selected from the group consisting of the colon, the rectum and the anal sphincter, c) implanting at least one powered restriction device in a position that enables it to at least partially restrict the movement of faeces through the rectum and/or anus, wherein said restriction device is used to decrease the cross sectional area of the faecal passageway in order to at least decrease the movement of faces through said passageway.

The method comprises steps normally carried out before, under and after surgery such as, but not limited to: preparing the patient for surgery, sedating the patient, monitoring sedation and waking up the patient.

In one embodiment, a laparoscopical method is used for surgery. In one embodiment the surgical step is combined with a coloscopic method to observe the patient.

In one embodiment a coloscopic method is used for placing a sensor in the patient. In one embodiment a coloscopic method is used for calibrating the restriction device.

In one embodiment the sensor is used to measure a parameter selected from the group consisting of an electrical parameter, pressure, volume, diameter, stretching, elongation, extension, movement, elasticity, muscle contraction, temperature, flow and nerve impulse.

In one embodiment, the restriction device is adjustable in order to allow defecation when the patient so needs, and then closing the restriction device in order to stop the movement of faeces. In one embodiment, the device is adjusted manually. In one embodiment the device is adjusted non-manually. Normally, the patient will herself determine when the manual adjustment will be used. In an alternative embodiment the device is adjusted automatically. Automatic release is in one embodiment and is only used in emergency situations, such as preventing rupture if the pressure becomes too high. That could occur, for example, if the patient loses consciousness.

In one embodiment the restriction device is adjusted from outside the body of the patient, for example by a remote control that is conveniently handled by the patient. In one embodiment the patient uses an implanted switch to control the restriction device. This is useful in case the remote control is lost or breaks down. Preferably the switch is implanted subcutaneously at a convenient location, which in one embodiment is a site which is placed at a distance from the restriction device.

In one embodiment the method comprises the additional step of placing in the body of the patient at least one sensor that measures at least one physiological parameter of the patient Examples of parameters include, but are not limited to: pressure, volume, diameter, stretching, elongation, extension, movement, elasticity, muscle contraction, temperature and nerve impulse. In one embodiment said sensor is adapted to sending an alarm signal to the patient.

In one embodiment the method comprises the additional step of implanting in the body of the patient at least one sensor that measures at least one functional parameter of said restriction device. The parameter is selected from the group consisting of an electrical parameter, pressure, volume, diameter, stretching, elongation, extension, movement, elasticity, temperature and flow. In one embodiment said sensor is adapted to sending an alarm signal to the patient.

In one embodiment more than one restriction device is implanted as to engage the rectum, colon or anal sphincter. Thus, in one embodiment, two or more restriction devises are implanted. In an alternative embodiment, one restriction device is designed as to restrict in more than one location. By using this approach optimal restriction of the movement of faeces can be achieved.

The method according to any of the embodiments could be adapted to comprise implanting at least one switch in the patient for manually and non-invasively controlling the restriction device. The energized system enables an operation device to operate the restriction device.

The method could, according to one embodiment, further comprise implanting a hydraulic device having an implantable hydraulic reservoir, which could be hydraulically connected to the restriction device. The restriction device could be adapted to be non-invasively regulated by manually pressing the hydraulic reservoir.

According to another embodiment, the method could further comprise using a wireless remote control for non-invasively controlling the restriction device. The wireless remote control could comprise at least one external signal transmitter and/or receiver, further comprising an internal signal receiver and/or transmitter implantable in the patient for receiving signals transmitted by the external signal transmitter or transmitting signals to the external signal receiver. The wireless remote control could further be adapted to transmit at least one wireless control signal for controlling the restriction device. The wireless control signal could comprise a frequency, amplitude, or phase modulated signal or a combination thereof. The wireless remote control could further be adapted to transmit an electromagnetic carrier wave signal for carrying the control signal.

According to another embodiment the method could comprise using a wireless energy-transmission device for non-invasively energizing the implantable energy consuming component of the restriction device with wireless energy. The wireless energy could comprise a wave signal, selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal, gamma radiation signal, an electric field, a magnetic field, a combined electric and magnetic field.

A control signal could comprise an electric field, a magnetic field, a combined electric and magnetic field. The signal could comprise an analogue signal, a digital signal, or a combination of an analogue and digital signal. For powering the energy consuming component of the restriction device, the implantable restriction device could comprise or be connected to an implantable internal energy source. According to another embodiment the method comprises an external energy source for transferring energy in a wireless mode, wherein the internal energy source is chargeable by the energy transferred in the wireless mode.

According to a further embodiment the method could further comprise implanting a sensor or a measuring device sensing or measuring a functional parameter correlated to the transfer of energy for charging the internal energy source, and a feedback device for sending feedback information from inside the patient's body to the outside thereof, the feedback information could be related to the functional parameter sensed by the sensor or measured by the measuring device.

According to yet another embodiment, the method could further comprise using a feedback device for sending feedback information from inside the patient's body to the outside thereof, the feedback information being related to at least one of a physical parameter of the patient and a functional parameter related to the restriction device.

The method could, according to one embodiment, further comprise implanting a sensor and/or a measuring device and an implantable internal control unit for controlling the restriction device in response to information being related to at least one of a physical parameter of the patient sensed by the sensor or measured by the measuring device and a functional parameter related to the restriction device sensed by the sensor or measured by the measuring device. The physical parameter could according to one embodiment be a pressure or a motility movement.

The method could, according to one embodiment, comprise using an external data communicator and an implantable internal data communicator communicating with the external data communicator, the internal communicator feeds data related to the restriction device or the patient to the external data communicator and/or the external data communicator feeds data to the internal data communicator.

The method according to any of the embodiments herein could further comprise using a motor or a pump for operating the restriction device, or a hydraulic operation device for operating the restriction device. The operation device could comprise a servo designed to decrease the force needed for the operation device to operate the restriction device instead the operation device acting a longer way, increasing the time for a determined action.

According to one embodiment the method could further comprise using an operation device for operating the restriction device and component connected thereto. The wireless energy could be used in its wireless state to directly power the operation device to create kinetic energy for the operation of the restriction device, as the wireless energy is being transmitted by the energy-transmission device. The method could also comprise using an energy-transforming device for transforming the wireless energy transmitted by the energy-transmission device from a first form into a second form energy.

The energy-transforming device could be adapted to directly power implantable energy consuming component of the restriction device with the second form energy, as the energy-transforming device transforms the first form energy transmitted by the energy-transmission device into the second form energy. Me second form energy could comprise at least one of a direct current, pulsating direct current and an alternating current. The energy of the first or second form could comprise at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

For protecting the restriction device and the component connected thereto, the method could further comprise implanting an implantable electrical component including at least one voltage level guard and/or at least one constant current guard. A control device could be arranged to control the transmission of wireless energy from the energy-transmission device, and an implantable internal energy receiver for receiving the transmitted wireless energy, the internal energy receiver could be connected to implantable energy consuming component of the restriction device for directly or indirectly supplying received energy thereto, the method could further comprise a determination device adapted to determine an energy balance between the energy received by the internal energy receiver and the energy used for the implantable energy consuming component of the restriction device, the control device could be adapted to control the transmission of wireless energy from the external energy-transmission device, based on the energy balance determined by the determination device.

The determination device could be adapted to detect a change in the energy balance, the control device could be adapted to control the transmission of wireless energy based on the detected energy balance change. Me determination device could in turn be adapted to detect a difference between energy received by the internal energy receiver and energy used for the implantable energy consuming component of the restriction device, and the control device could be adapted to control the transmission of wireless energy based on the detected energy difference.

The energy-transmission device could comprise a coil placed externally to the human body, which in turn could further comprise an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power. The electric circuit could be adapted to deliver the electrical pulses to remain unchanged except varying the first and/or second time intervals.

The method could according to one embodiment comprise using an electric circuit having a time constant which is adapted to vary the first and second time intervals only in the range of the first time constant, so that when the lengths of the first and/or second time intervals are varied, the transmitted power over the coil is varied.

The implantable internal energy receiver for receiving wireless energy could comprise an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmit wireless energy which is received by the first coil of the energy receiver, the method further comprises using a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

The method could also comprise implanting and internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the method further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

In the embodiments in which the method comprises using an external second coil, the external second coil could be adapted to be moved in relation to the internal first coil to establish the optimal placement of the second coil, in which the coupling factor is maximized. The external second coil could also be adapted to calibrate the amount of transferred energy to achieve the feedback information in the determination device, before the coupling factor is maximized.

In one embodiment the surgical procedure is carried out with a laparoscopical procedure. In one embodiment the laparoscopial procedure is carried out after the surgical site has been insufflated with a gas.

In one embodiment at least one trocar is used. In one embodiment at least two trocars are used. In one embodiment at least one trocar with a diameter from 5 to 12 mm is used.

In one embodiment at least one laparoscopic trocar is inserted through the vaginal wall of the patient, and the dissection is performed using at least one dissecting tool which is inserted through the trocar.

In one embodiment the method comprises the following steps: a) inserting a tube or needle into the body of the patient, b) using the tube or needle to insufflate a site of the body of the patient with a gas c) inserting at least two laparoscopic trocars into said site, d) inserting at least one camera trough at least one laparoscopic trocar, and e) inserting at least one dissecting tool through at least one laparoscopic trocar, In one embodiment the method comprises the additional step of fixating said restriction device. In one embodiment the restriction device is fixed in the adjacent tissue.

In one embodiment the restriction device is fixated by creating a tunnel from a part of the colon.

In one embodiment the method comprises the additional step of suturing in layers.

In one embodiment the method comprises the additional step of stimulating contraction by using electricity in at least one selected from the group consisting of a) the colon, b) the rectum, c) the anal sphincter and d) muscle surrounding said organs. In one embodiment the method comprises the additional step of stimulating in more than one location of the restriction device.

Restriction Device

In a second aspect the invention provides an implantable restriction device for the treatment of anal incontinence in women that engages the colon or rectum by forming a loop around the colon or rectum characterised in that said device can adapt a straight conformation during implantation of the device and a loop conformation when the device is implanted and engaging the colon or rectum, and where said straight conformation has a) surface with low friction relative to body tissue, b) has a shape that is streamlined with respect to movement in the direction of the main axis of the device in its straight conformation.

In one embodiment at least one end of the straight conformation is rounded, pointed or streamlined. In one embodiment the streamlined shape is achieved by the restriction device lacking protruding portions. In one embodiment the low friction is obtained by coating at least a part of the device with a lubricating compound. In one embodiment the low friction surface is obtained by the device having a surface made of smooth plastic.

In one embodiment at least one end of the straight conformation has an attachment structure for attaching a surgical instrument. In one embodiment the attachment structure comprises a fast coupling.

Examples of embodiments of the restriction device include but are not limited to U.S. Pat. No. 7,367,938 and EP 1 255 511.

Further aspects and embodiments are defined in the appended claims, which are specifically incorporated herein by reference.

Other features and uses of the invention and their associated advantages will be evident to a person skilled in the art upon reading the description and the examples.

It is to be understood that this invention is not limited to the particular embodiment shown here. The following examples are provided for illustrative purposes and are not intended to limit the scope of the invention since the scope of the present invention is limited only by the appended claims and equivalents thereof.

Please note that any embodiment or part of embodiment or feature or method or associated system or part of system described herein may be combined in any combination.

Definitions

Before the invention is disclosed and described in detail, it is to be understood that this invention is not limited to particular surgical steps, configurations, method steps, substrates, and materials disclosed herein as such surgical steps, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that as used in this specification and the appended claims, the singular forms "a", "an" and "the" include plural referents unless the context clearly dictates otherwise.

If nothing else is defined, any terms and scientific terminology used herein are intended to have the meaning commonly understood by those of skill in the art to which this invention pertains.

The term "about" as used in connection with a numerical value throughout the description and the claims denotes an interval of accuracy, familiar and acceptable to a person skilled in the art. Said interval is ±10%.

As used herein, the following terms refers to the following:

"anal incontinence" refers to inability to control discharge of faeces,

"urinary incontinence" refers to inability to control discharge of urine,

"consumed energy" refers to energy consumed by a system,

"energy balance" refers to the difference between two measurements of energy,

"received energy" refers to energy received by a system by means energy transfer method, "rectum" refers to the rectum, the anal canal and the anal sphincter, "restriction device" refers to a device that is able to at least decrease the flow through a tubular organ, "transmitted energy" refers to energy transmitted from a system by means of an energy transfer method.

"restriction device and components connected thereto" includes the restriction device and any operating device, energy receiver, determination device, energy-transforming device, switches and other component connected (wireless or not) to the restriction device whether electrical, mechanical or hydraulical.

"system" refers to the restriction device and component connected thereto includes the restriction device and any operating device, energy receiver, determination device, energy-transforming device, switches and other component connected (wireless or not) to the restriction device whether electrical, mechanical or hydraulic.

It should be understood that the planes referred to in this application are all imaginary planes.

BRIEF DESCRIPTION OF THE DRAWINGS

The invention is described with reference to the drawings in which:

FIGS. 5a-h shows a surgical instrument according to the invention.

FIGS. 15-29 schematically show various embodiments of the system for wirelessly powering the restriction device and component connected thereto shown in FIG. 14.

DETAILED DESCRIPTION AND DESCRIPTION OF THE DRAWINGS

Figure 1:
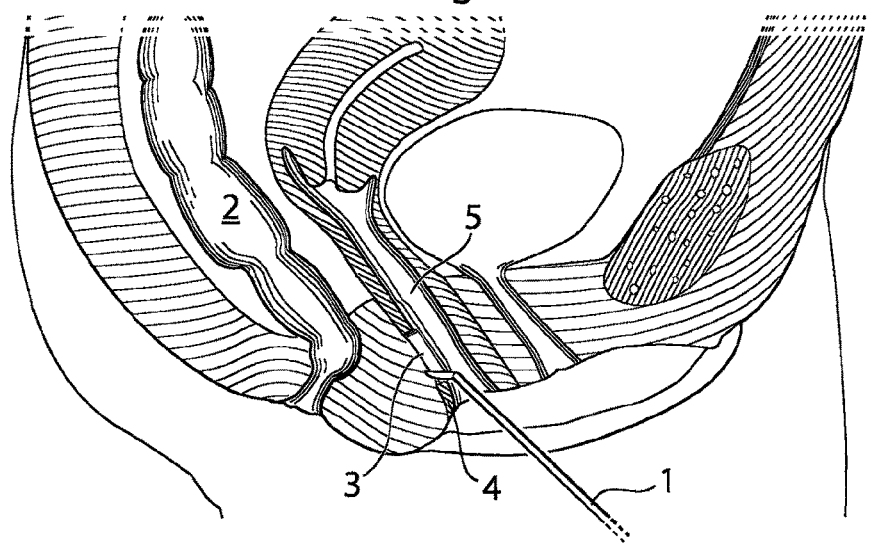
FIG. 1-3 shows a surgical method whereby a restriction device is placed as to engage the rectum by accessing the rectum trough an incision in the vagina.

FIG. 1 shows how a surgeon uses a surgical tool 1 to access the rectum or colon 2 through an incision 3 in the wall 4 of the vagina 5 of the patient.

Figure 2A:
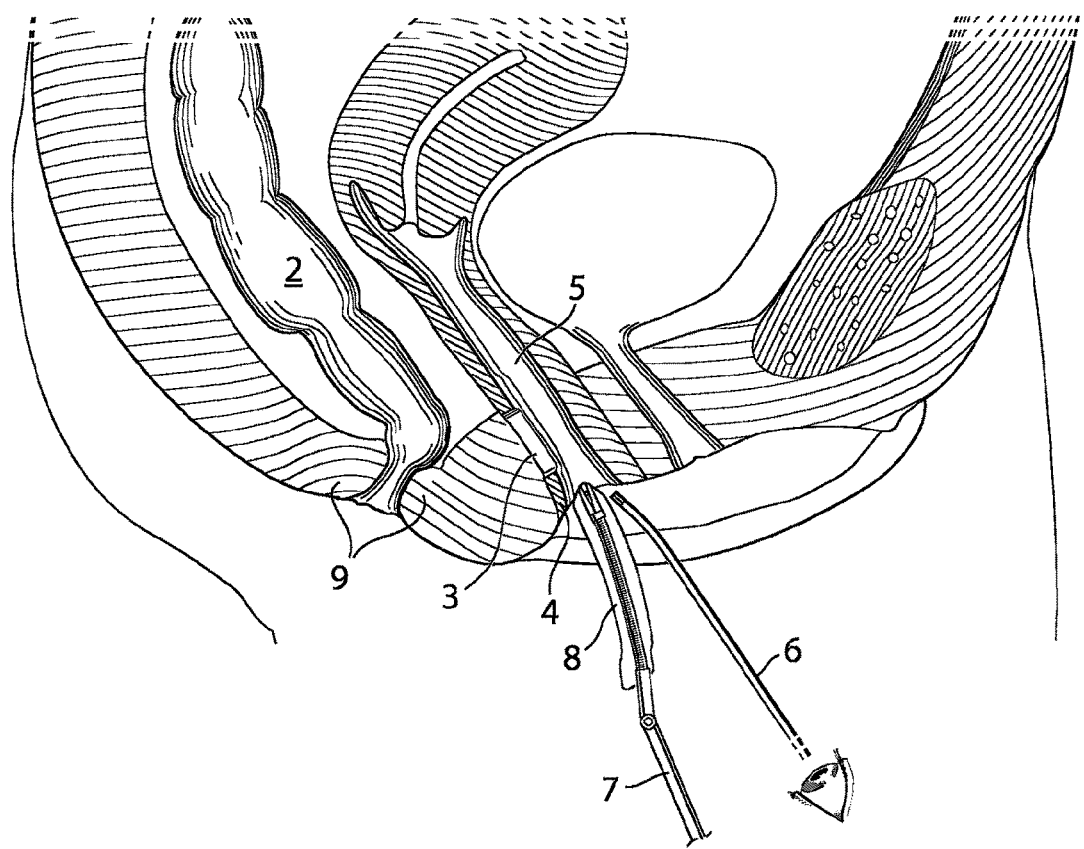

FIG. 2a shows a subsequent step of the method, where a viewing scope 6 has been inserted through the incision 3 in the wall 4 of the vagina 5. The viewing scope allows the surgeon to carry out surgical procedures in a minimally invasive manner. A surgical instrument 7, which is described in detail below, is used for dissecting the area 9 around the rectum 2 to enable the implantation of the restriction device 8. FIG. 2a shows how the surgical instrument 7 is used for introducing the restriction device 8 in its open conformation into the vagina for subsequent insertion to the correct place in a manner described in more detail below.

Figure 2B:
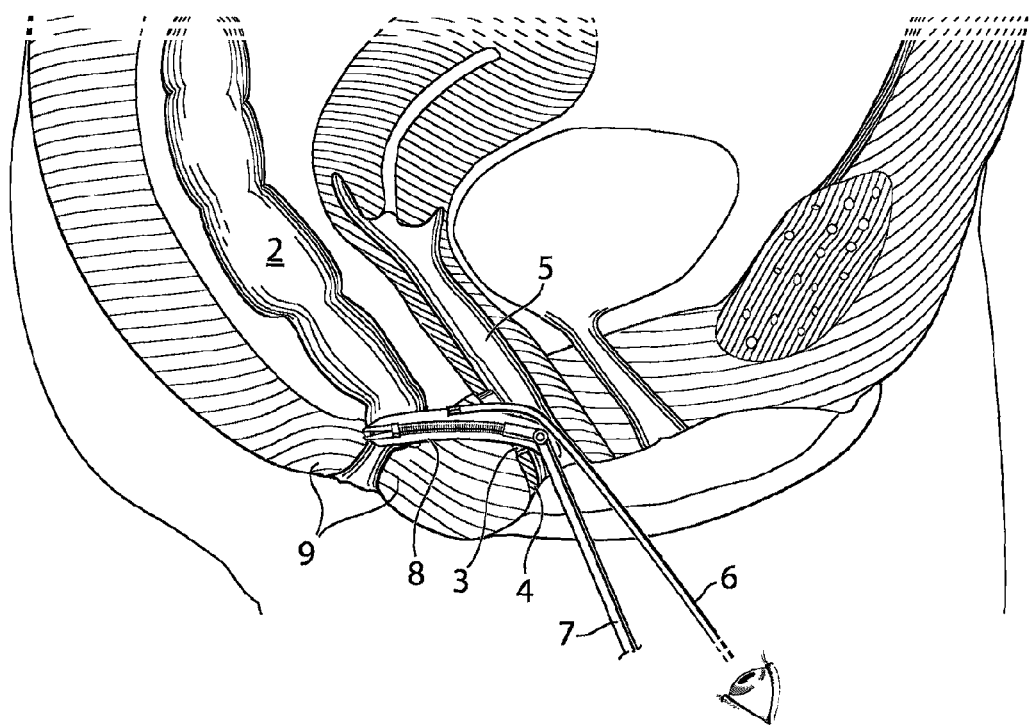

FIG. 2b shows the next step of the method, where the surgical instrument 7 has brought the restriction device 8, which is still in its open conformation, though an incision 3 in the wall 4 of the vagina 5, to the rectum 2.

Figure 3:
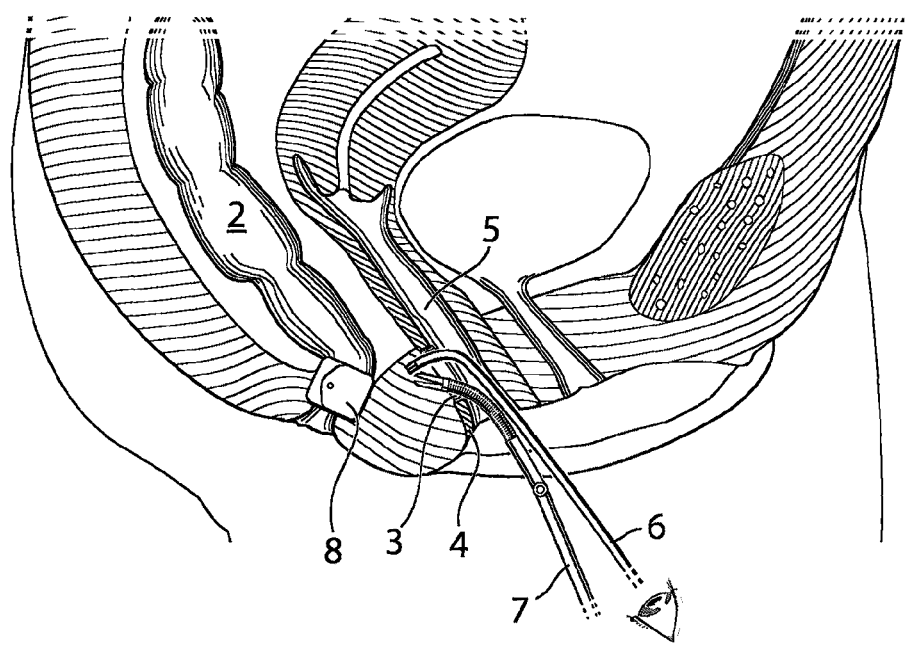

FIG. 3 shows an even later step in the surgical procedure. The restriction device 8 is now in place engaging the rectum 2 and the surgical instrument 7 is being retracted. The restriction device is now in its closed conformation. Other devices that are to be connected to the restriction device such a control device, a switch, a energy source and a sensor can be implanted and connected to the restriction device during the same procedure, if desired.

Figure 4:
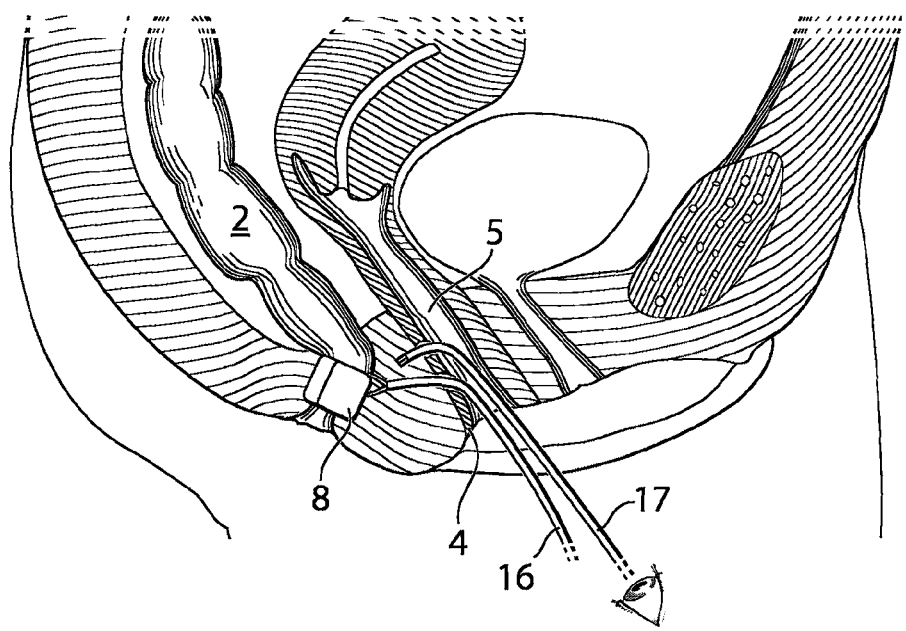
FIG. 4 shows an embodiment of the method where a laparoscopic method is used.

FIG. 4 shows en embodiment of the invention where a laparoscopical method is used for carrying out the implantation of the restriction device. Laparoscopic procedures involve percutaneously accessing an internal surgical site with small-diameter access tubes (typically 5 to 12 mm diameter), usually referred to as laparoscopic trocars, which penetrate the skin and permit access to the surgical site. A viewing scope is introduced through at least one laparoscopic trocar and the surgeon performs surgery using instrument inserted through other appropriately placed laparoscopic trocar(s) while viewing the operative site on for instance a video monitor connected to the viewing scope. The surgeon is thus able to perform a wide variety of surgical procedures requiring only a few 5 to 12 mm punctures at the surgical site. Consequently, patient trauma and recovery time are greatly reduced. Laparoscopic procedures involve the insufflation of the surgical site with gas in order to create sufficient operating space to perform a desired procedure. Usually more than one trocar is used.

In FIG. 4, trocars are inserted in the vagina 5 and trough the wall of the vagina of the patient in order to access the rectum 2. One trocar 16 is used for placing a restriction device 8 around the rectum 2 and one trocar 17 is used for inserting a viewing scope or a camera for observing the rectum 2 from the outside.

FIG. 5a shows a surgical instrument 7 according to the invention. The instrument is used for being held by the surgeon, being inserted through an incision in the wall of the vagina so that it reaches a portion of the rectum or colon where the restriction device is going to be implanted, dissecting a portion of the rectum or colon so that the instrument, which can form a loop, can reach around the rectum or colon. The instrument is then connected to the restriction device and the restriction device is then in its straight conformation. The instrument is then retracted, pulling the restriction device in place behind the rectum or colon. The restriction device is then closed to form a loop around the rectum or colon.

The instrument 7 comprises a main part with a handle 21 on to which an elongated member 23 is mounted at an adjustable angle A between the main part of the instrument 21 and the elongated member 23 of from 0° to less than 180° to the main part of the instrument 21. In one embodiment the elongated member 23 is connected to the main part of the instrument by a joint 42 such that the angle A between the main part of the instrument and the elongated member is variable. The main part of the instrument 21 is preferably elongated in order for the surgeon to reach the rectum and/or colon through an incision in the vagina.

The flexible tip 24 of the elongated member 23 is flexible and can change conformation from an essentially straight conformation to a loop or hook conformation as seen in FIG. 5b-5c. In one embodiment this is achieved by a flexible gooseneck that is essentially smooth.

The joint 42 has a pivotal axis, wherein the first angle A between the main part of the instrument and the elongated member is between 20 and 180 degrees. A first plane 42' has a definition so that it extends perpendicularly to the pivotal axis, i.e., so that the elongated main part and the elongated member lies in this first plane.

The flexible tip 24, when in the loop or hook conformation, defines an opening with an axial hole going there through A second plane 24' extends perpendicularly to the axial hole through said loop or hook, so that the flexible tip 24, in it loop or hook conformation, lies in this second plane.

The orientation of the first plane 42' is different from the orientation of the second plane 24'. In other words, the normals or perpendiculars of the first and second planes are direct in different directions. Thereby a flexible instrument for accessing an opening in the vaginal wall of the patient is provided.

The definition of the angle or orientation differences between the planes is described as the closest and thereby smallest angle.

In one embodiment, the flexible tip 24 can move in any direction. The loop does not necessarily have to form a closed circle but preferably a large enough portion of a circle, forming a hook, so that the attachment structure 26 protrudes from the other side of the rectum or colon when the flexible tip 24 surrounds the rectum or colon. Preferably the loop forms 270 degrees of a circle, or more. The flexibility of the flexible tip 24 can be achieved in different manners that are disclosed by prior art. The change in conformation can be carried out mechanically, i.e. by muscle power or by a powered device, in one embodiment. In one embodiment, the bending of the flexible tip 24 is controlled by a means selected from the group consisting of a mechanical manipulation, an electric control device and a hydraulic fluid system. In one embodiment, the control of the bending of the flexible tip 24 is achieved by at least two parallel wires that run inside the flexible tip 24, where one end of each wire is connected to the head 25 and one end of the wire is connected to the elongated member 23, and tension can be applied to each of the wires independently. The instrument has one device 40 for manoeuvring the bending of the flexible tip 24 and one switch 41 for controlling the attachment structure 26. In one embodiment the flexible tip 24 is connected to the elongated member by a ball-and-socket joint. This makes it possibly to use the instrument from right to left or from left to right, depending on the preferences of the surgeon.

The head 25 of the flexible tip 24 has two functions. It comprises a tissue dissector 27 and an attachment structure 26 for the restriction device. Alternatively or additionally, the head of the flexible tip may be adapted for attachment of a camera (not shown in the figures) for assisting the movement of the flexible tip into the patient.

The dissector is adapted for dissecting soft tissue and passing through the tissue surrounding the rectum or colon. Although the flexible tip 24 is flexible it is still rigid enough to be used to dissect the area around the rectum or colon. The tissue surrounding the rectum and colon consists mostly of fibrotic tissue and fat tissue that is comparatively soft and can be dissected by using a blunt instrument.

The loop conformation of the flexible tip 24 of the surgical instrument 7 is adapted to reach around the rectum or colon and thus has an inner diameter that is larger than the outer diameter of the rectum or colon. In one embodiment the loop has an inner diameter of 1-12 cm, preferable 5-7 cm.

Figure 5D:
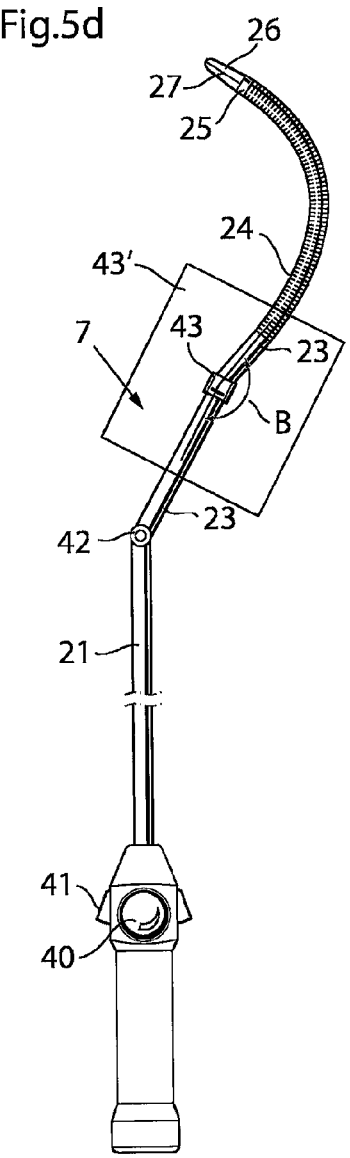
Figure 5E:
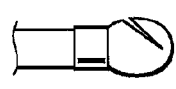
Figure 5F:
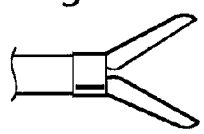
Figure 5G:
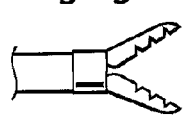
Figure 5H:
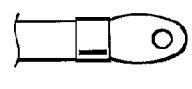

FIG. 5d shows a different embodiment of the surgical instrument. Here, the elongated member 23 is equipped with an additional joint 43 having a pivotal axis that facilitates the bending of the elongated member 23 around a body lumen (such as the rectum or the urethra). The additional joint 43 introduces a second angle (B) between the parts of the elongated member 23 separated by joint 43. The angle (B) can retain the same values as angle (A), but can be adjusted separately there from with the joint 43. The additional joint increases the flexibility when operating the surgical instrument. Both Angle A and B and thereby joint 42 and 43 may in a special embodiment be rotated before it is angled thus allowing 360° or less turn-around. The instrument may otherwise disclose the same features as in 5c.

A third plane 43' is defined as extending perpendicularly to the second pivotal axis, so that the two part of the elongated member lie in this third plane. The orientation of this third plane 43' is so that it is different from the orientation of the first plane 42' or the second plane 24', see FIG. 5c, or preferably both the first plane and the second plane, thereby increasing the flexibility of the instrument.

The head 25 of the flexible tip 24 comprises an attachment structure 26 for reversibly associating the instrument with an implantable restriction device. Various embodiments of the attachment structure 26 are shown in FIGS. 5c-f. Thus the attachment structure 26 is selected from a notch where a string can be attached (5c), a pincer (5d), a toothed pincer (5e) and a noose (50). In one embodiment the attachment structure 26 of the instrument 7 comprises a coupling that can be associated with a corresponding coupling on the restriction device 8. In one embodiment the attachment structure 26 of the instrument 7 comprises a fast coupling.

Figure 6A:
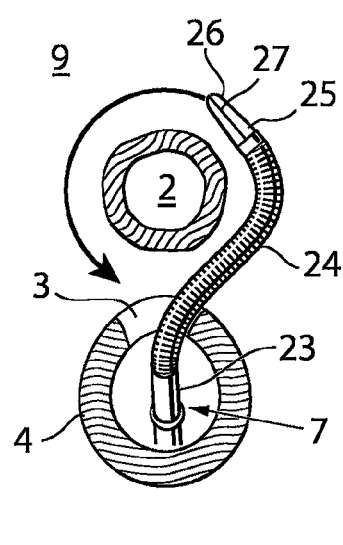
FIGS. 6a-d shows the use the surgical instrument in FIG. 5.
Figure 6B:
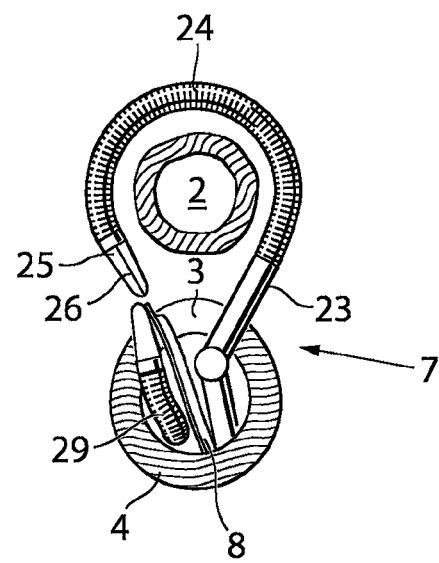

FIGS. 6a-d shows one intended use of the surgical instrument 7. This is just one example and the angle A or B is preferable turned in relation to the disclosed example. First an incision 3 is made in the vagina of the patient. Then the elongated member 23 and the flexible tip 24 of the instrument 7 are inserted through the incision 3. The tissue dissector 27 of the end 25 of the flexible tip 24 is used to push through the tissue 9 surrounding the rectum or colon 2 as shown in FIG. 6a. When the flexible tip 24 has reached behind the rectum or colon 2 it is slightly bent so that it can dissect behind the rectum or colon 2. The flexible tip 24 is then slightly bent and moved inwards so that it can reach even further behind the colon or rectum 2 until the attachment structure 26 of the head 25 of the flexible tip 24 protrudes from the other side of the rectum or colon as shown in FIG. 6b. The restriction device 8, which is in it straight conformation, is brought into the site of surgery with the means of another instrument 29. The attachment structure 26 of the surgical instrument 7 is then attached to the restriction device 8.

Figure 6C:
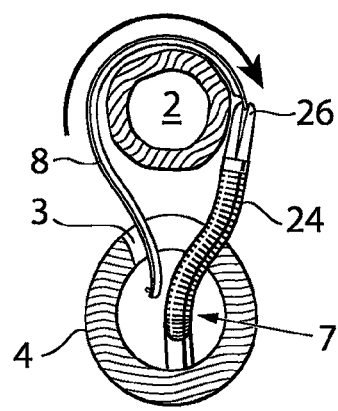
Figure 6D:
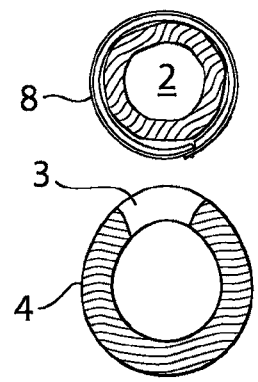

The flexible tip 24 is then retracted by performing the reverse movement, thereby pulling the restriction device 8 in place behind the colon or rectum 2 as shown in FIG. 6c. The restriction device 8 is now essentially in place and is detached from the attachment structure 26 of the surgical instrument 7. The restriction device 8 is then closed to form a loop around the rectum 2 as seen in FIG. 6d.

In one embodiment, essentially seen in FIGS. 2a and 2b, the device 8 is attached to the instrument 7 before the flexible tip 24 is brought in behind the colon or rectum 2. In this embodiment, the device 8 is brought in place as the flexible tip 24 bends around the colon or rectum 2 and the additional instrument 29 is not needed.

In one embodiment the instrument 7 comprises a viewing scope allowing implantation of the device to be carried out with a minimally invasive procedure.

The surgical instrument 7 is in one embodiment used for implanting devices that are associated with the restriction device, such as a control device for controlling the adjustment of the restriction device, and devices for powering the device and for storing energy. Also, in one embodiment, switches sensors and leads are implanted. In one embodiment, more than one restriction device is implanted.

Figure 7:
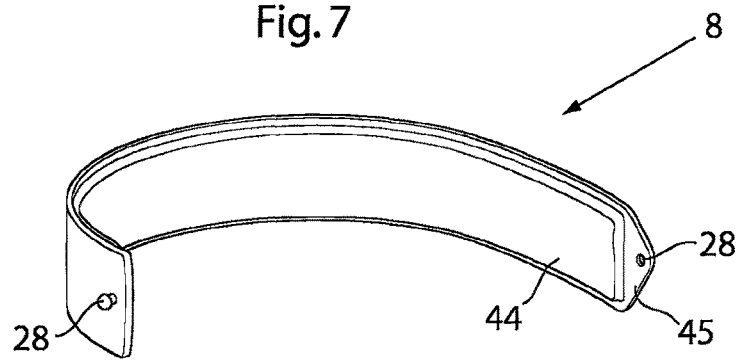
FIG. 7 is an example of a restriction device according to the invention.

FIG. 7 shows a restriction device 8 according to the invention. The restriction device is flexible and can change conformation from being essentially straight to being a loop with an inner circumference of a size such that it engages the rectum or colon. The restriction device 8 has a smooth surface 44 without protruding park that makes it adapted to be dragged around behind the rectum or colon by the surgical instrument without snagging or getting stuck. In one embodiment it is pointed, rounded or streamlined making it suitable for being pulled in place without damaging the colon or rectum or surrounding tissues. Thus, at least one end 45 of the restriction device is pointed. Furthermore, in one embodiment, the restriction device 8 has locking mechanism 28 whereby it can be made to form a loop. Preferably the locking mechanism is of a self-lock type.

In one embodiment at least one end 45 of the restriction device 8 has an attachment structure adapted to be reversibly associated with the attachment structure 26 of the surgical instrument 7. In one embodiment this is a fast coupling.

Figure 8:
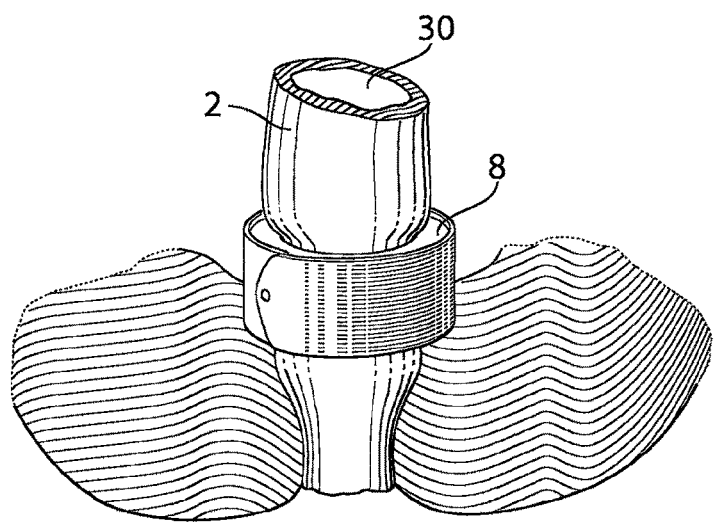
FIG. 8 shows the restriction device when it has been implanted and is engaging the rectum of a patient.
Figure 9:
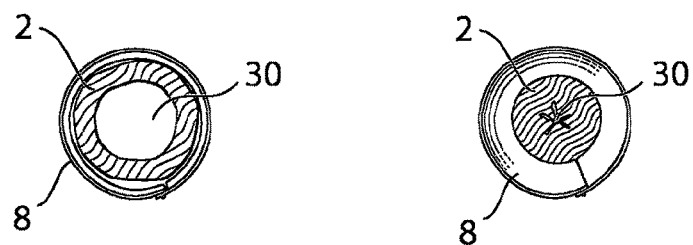
FIGS. 9a-b shows open and closed states, respectively, of the restriction device when implanted to engage the rectum of a patient.

FIG. 8 shows the restriction device 8 in place as it is engaging the rectum 2. The restriction device 8 forms a loop around the rectum 2. The inner diameter)of the loop is adjustable, thereby opening or closing the rectum as seen in FIG. 9a and FIG. 9b where FIG. 9a shows the open state and 9b shows the closed state where the lumen 30 of the colon or rectum 2 is essentially extinct. The change in diameter is carried out by mean selected from a hydraulic mean and a mechanical mean well known to the person skilled in the art Examples of prior art include but are not limited to U.S. Pat. No. 7,367,938 and EP 1 255 511. In the embodiment shown in FIG. 9 the change of diameter is achieved by a hydraulic mean.

Coloscopy is a technology that involves inserting a probe with a camera in the colon of the patient. This enables the operator to visually inspect the rectum or the colon. In one embodiment the surgical procedure is combined with coloscopy. This enables the surgeon to observe the lumen of the colon or rectum while surgery is being performed. This is used to, for example, see how much the rectum contract when the restriction device is engaged and allows for the verification of the correct positioning of the restriction device.

Figure 10:
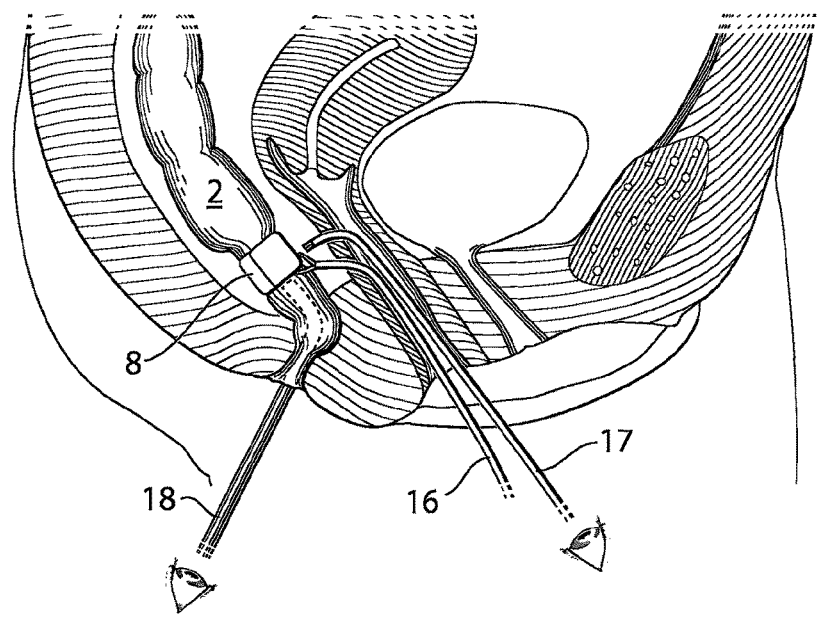
FIG. 10 shows how coloscopy is combined with a minimally invasive method for placing a restriction device on the colon.

FIG. 10 shows how a coloscope 18 is inserted through the rectum 2 enabling the surgeon to observe the interior of the rectum 2, while using trocars 16, 17 for placing a restriction device 8 as to engage the colon 2 and for observing the colon 2 from the outside. Furthermore, in one embodiment coloscopy is used for placing a sensor in the patient. In one embodiment, the sensor measures an electrical parameter. In an alternative embodiment the sensor measures at least one parameter from the group consisting of pressure, volume, diameter, stretching, elongation, extension, movement, elasticity, muscle contraction, temperature, flow and nerve impulse. In one embodiment output from the sensor is used for calibrating the restriction device. In the embodiment shown in FIG. 10 the restriction device is placed as to engage the colon rather than the rectum.

In one embodiment the restriction device is fixed in the body of the patient. In one embodiment this is done by fixating the restriction device in the adjacent tissue. In one embodiment the restriction device is fixed in the patient by creating a tunnel of tissue from the colon or rectum of the patient. After fixating, the incision(s) in the patient is closed. In one embodiment this is achieved by suturing in layers. If a minimally invasive procedure has been used, the incision may be so small that other means are used. Examples include, but are not limited to, stapling and taping.

The rectum, the colon and the anal sphincter are equipped with muscle tissue that is able to contract and thus control the movement of faeces. Dysfunction of this capacity can be one cause of anal incontinence. However, the capacity of muscle tissue to contract may be partially or completely restored by stimulating the muscle tissue with electricity. In one embodiment the method comprises stimulating contraction of the muscles surrounding the rectum, colon and/or anal sphincter by using electricity. In one embodiment, the stimulation takes place in more than one location of the restriction device.

Figure 11:
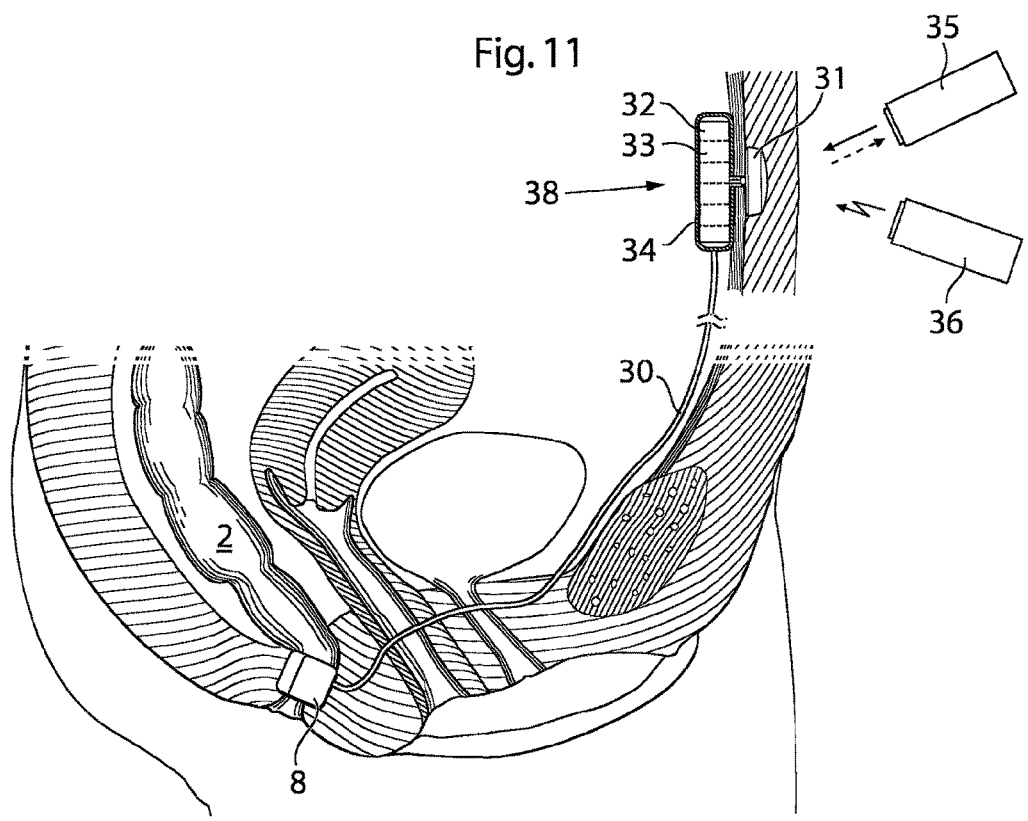
FIG. 11 shows how the restriction device is combined with a control device, a remote control an external energy source.

FIG. 11 shows the restriction device 8 implanted as to engage the rectum 2. It is adjustable and connected to the control device 38 by a power and control cord 30. The control device may comprise a subcutaneous switch 31, a receiver for wireless energy 32, a battery 33, a receiver 34 for energy and a remote control 35. Wireless energy is transmitted by a transmitter 36.

Figure 12:
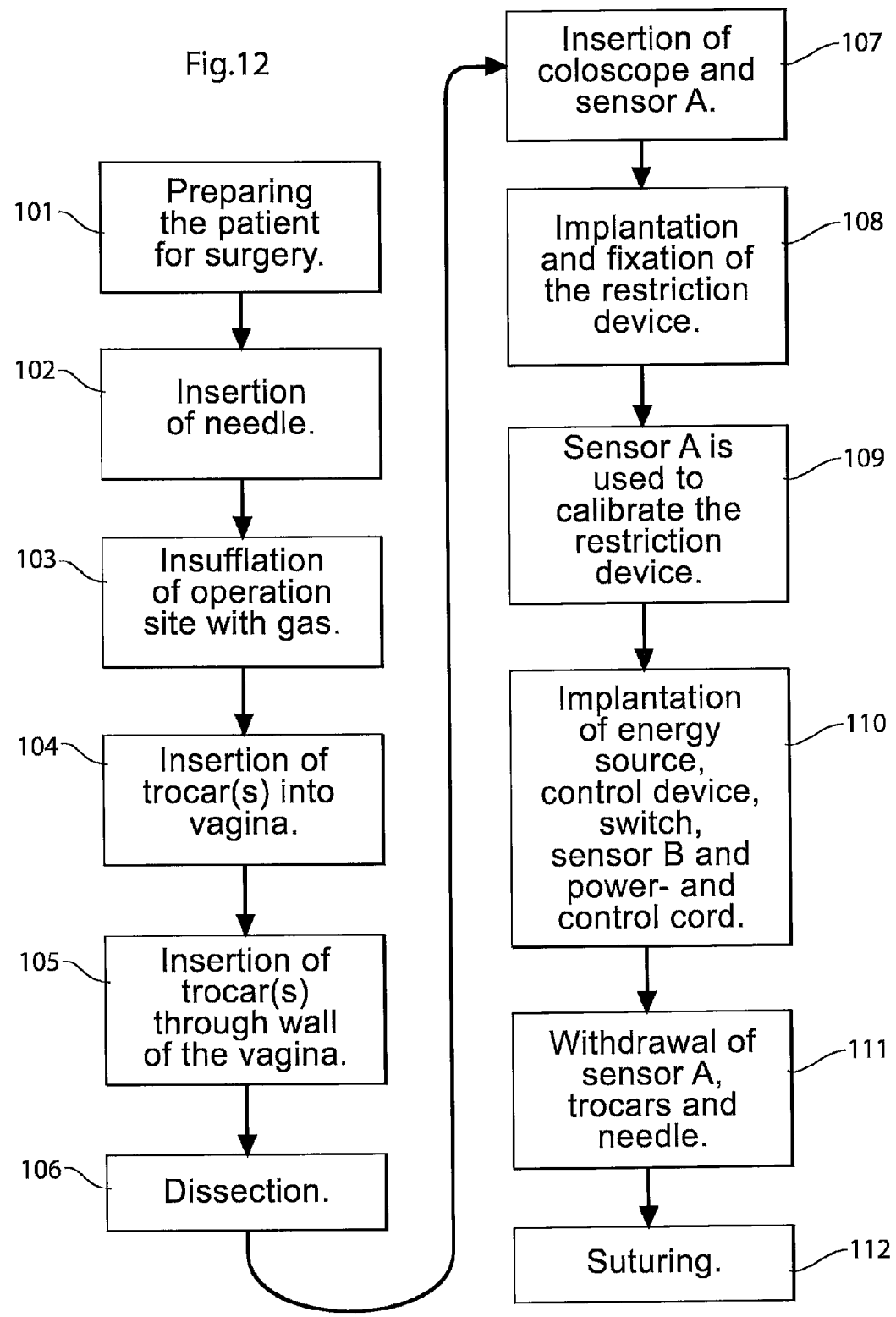
FIG. 12 is a flow chart that describes a method for treatment of a female patient suffering from anal incontinence involving a laparoscopic surgery method.

FIG. 12 is a flow chart showing one embodiment that includes several of the steps of the disclosed method where a laparoscopic method for surgery is used. In other embodiment, one or more steps may be omitted or performed in a different order. In step 101, the patient is prepared for surgery in a manner that is known to a person skilled in the art. In one embodiment the method is performed on the patient in the supine position. In step 102 a needle is introduced into the site of operation. In step 103, the site of operation is insufflated with a gas so that the site of operation is expanded. Step 104 is the insertion into the vagina of trocars. At least one trocar is used for viewing the operation site and at least one trocar is used for performing various surgical steps. The trocars are then in step 105 inserted through the wall of the vagina. In one embodiment, the trocars are inserted through the posterior wall of the vagina. The tips of the trocars are brought up to site of surgery which is the outside of the colon and/or rectum. Step 106 is dissection of the colon and/or rectum. A coloscope is then, in step 107, inserted through the anus. In one embodiment a sensor (sensor A in the figure) is introduced by using the coloscope. The coloscope is used to observe the rectum and/or colon from the inside during step 108, which is the implantation of the restriction device so that it engages the rectum and/or colon. By viewing the rectum and colon from the inside with the coloscope, the surgeon can ensure that the restriction device engages the rectum and/or colon in a correct manner. The restriction device is fixated in the surrounding tissue of the patient in step 108. Sensor A is used in step 109 to calibrate the restriction device. Sensor A is then removed from the patient. In step 110, other part are implanted in the patient, such as, but not limited to, an energy source, a control device and a switch. These may be included in the same subcutaneous implant A control cord, that connects the restriction device to the control device, and sensor B, are also implanted, in one embodiment. Step 111 is the withdrawal of the trocars, the coloscope and sensor A. In step 112 the incisions are closed by suturing or other means, such as taping, clamping or stapling. In one embodiment, step 109 is omitted. In one embodiment step 107 is omitted. In one embodiment, step 107 is carried out before step 106. In one embodiment, step 110 is carried out before step 109.

Figure 13:
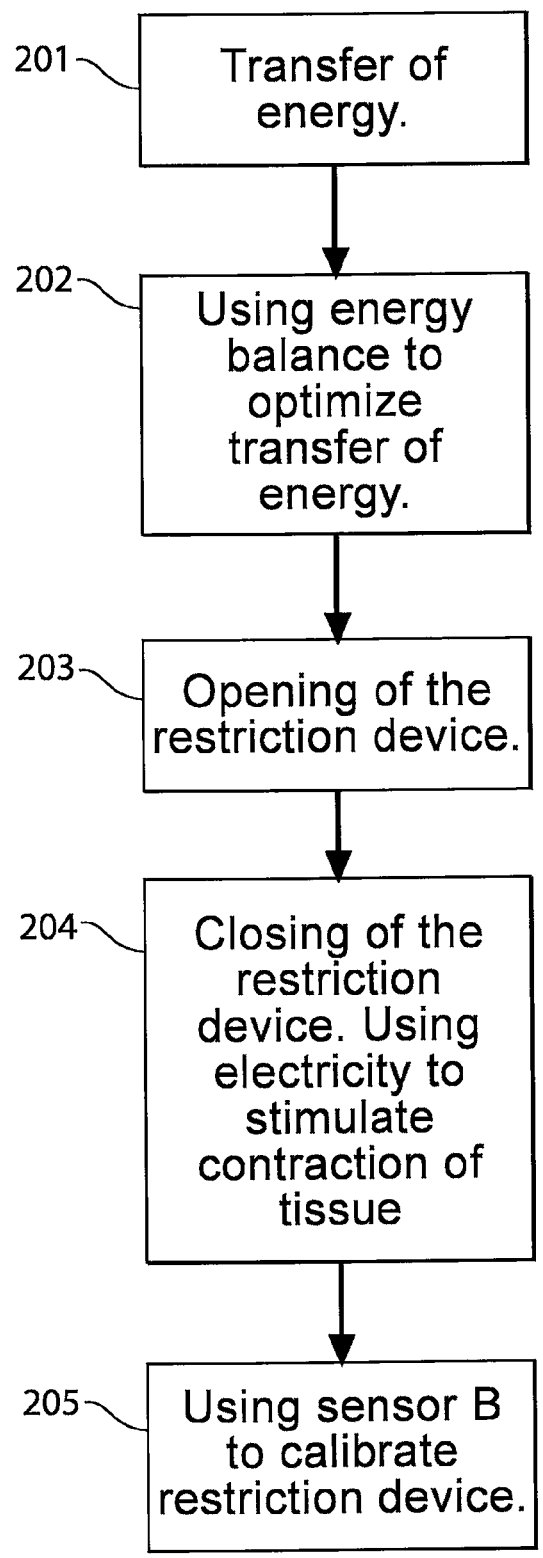
FIG. 13 is a flow chart showing how the method for treating a female patient suffering from anal incontinence is used postoperatively.

FIG. 13 shows one embodiment of how the method is used postoperatively, where the implanted parts are used to control defecation in an anal incontinent patient. This is one example of an embodiment only, and one or more steps may be omitted or performed in a different order. In step 201, energy is transferred to the energy source. In step 202, the energy balance is used to optimize the transfer of energy. In step 203, the patient opens the restriction device to allow defecation. In step 204, the restriction device is closed after the patient has finished defecation. Simultaneously, electricity is used to stimulate contraction of muscles of the rectum or colon. In step 205, the implanted sensor Bis used to calibrate the restriction device. In one embodiment step 205 is omitted. In one embodiment, step 205 is carried out before step 203.

Figure 14:
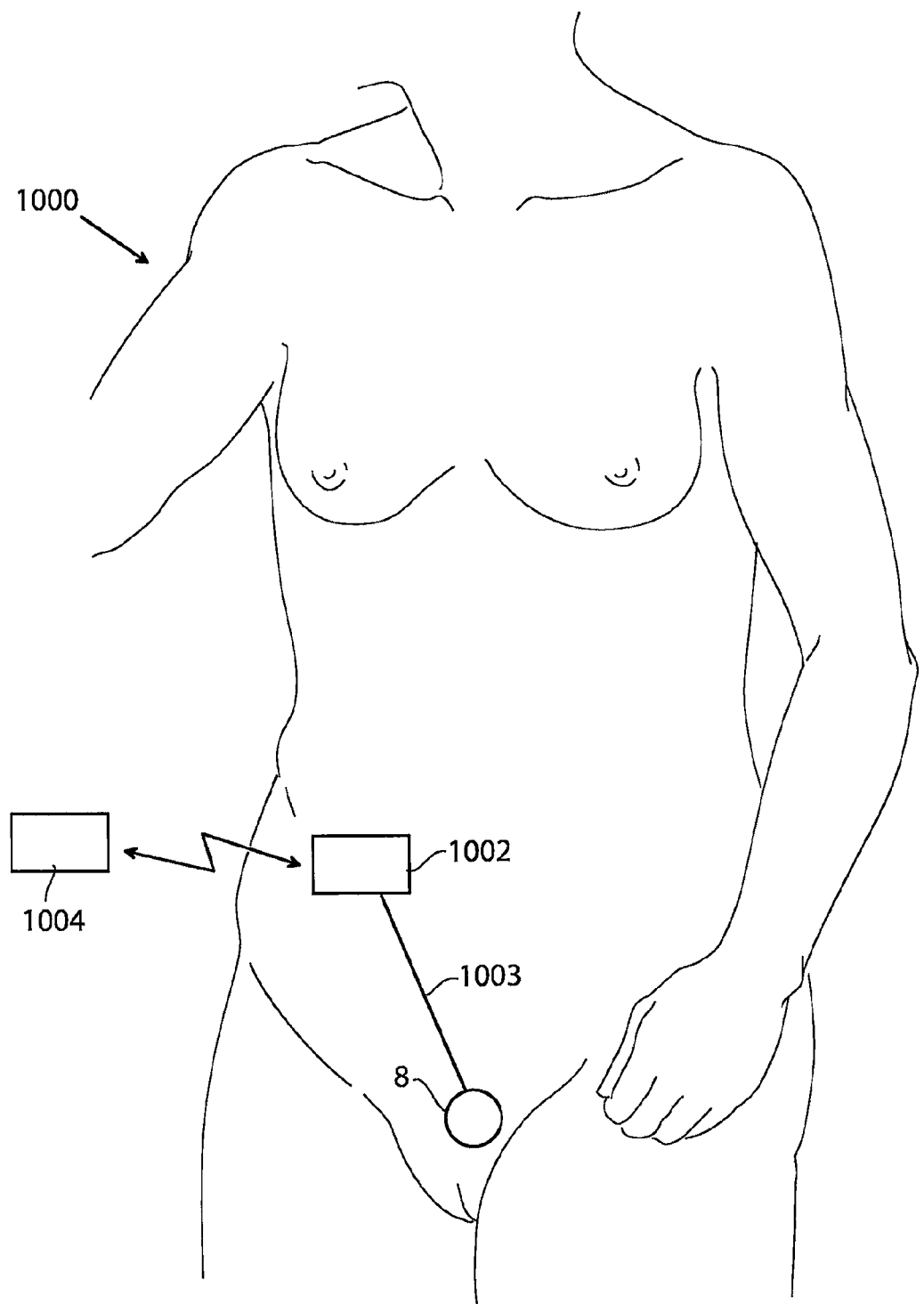
FIG. 14 illustrates an overview of the restriction device with components connected thereto comprising a system.

FIG. 14 illustrates a method for treating a disease comprising the implantation of a system 1000 comprising a restriction device 8 of the present invention, in the patient. An implanted energy-transforming device 1002 is adapted to supply energy consuming component of the restriction device 8 with energy via a power supply line 1003. An external energy-transmission device 1004 for non-invasively energizing the restriction device 8 transmit energy by at least one wireless energy signal. The implanted energy-transforming device 1002 transforms energy from the wireless energy signal into electric energy which is supplied via the power supply line 1003.

The implanted energy-transforming device 1002 may also comprise other component, such as: a coil for reception and/or transmission of signals and energy, an antenna for reception and/or transmission of signals, a microcontroller, a charge control unit, optionally comprising an energy storage, such as a capacitor, one or more sensors, such as temperature sensor, pressure sensor, position sensor, motion sensor etc., a transceiver, a motor, optionally including a motor controller, a pump, and other parts for controlling the operation of a medical implant.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted restriction device 8 is operable in response to the energy of the second form. The energy-transforming device 1002 may directly power the restriction device 8 with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the restriction device 8 and any component connected thereto, as the wireless energy is being transmitted by the energy-transmission device 1004. Where the system comprises an operation device for operating the restriction device 8, as will be described below, the wireless energy transmitted by the energy-transmission device 1004 may be used to directly power the operation device to create kinetic energy for the operation of the restriction device.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the restriction device 8 comprises electric component that are energized with electrical energy. Other implantable electric component of the system may be at least one voltage level guard or at least one constant current guard connected with the electric component of the restriction device 8.

Optionally, the energy of the first form and the energy of the second form may comprise magnetic energy, kinetic energy, sound energy, chemical energy, radiant energy, electromagnetic energy, photo energy, nuclear energy or thermal energy. Preferably, the energy of the first form and the energy of the second form are non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the restriction device 8. Alternatively, the energy-transmission device is controlled from outside the patient's body to release non-magnetic wireless energy, and the released non-magnetic wireless energy is used for operating the restriction device 8.

The external energy-transmission device 1004 also includes a wireless remote control having an external signal transmitter for transmitting a wireless control signal for non-invasively controlling the restriction device 8. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmit an electromagnetic carrier wave signal for carrying the digital or analogue control signals.

FIG. 15 illustrates the system 1000 of FIG. 14 in the form of a more generalized block diagram showing the restriction device 8, the energy-transforming device 1002 powering the restriction device 8 via power supply line 1003, and the external energy-transmission device 1004, The patient's skin 1005, generally shown by a vertical line, separates the interior of the patient to the right of the line from the exterior to the left of the line.

FIG. 16 shows an embodiment of the invention identical to that of FIG. 15, except that a reversing device in the form of an electric switch 1006 operable for example by polarized energy also is implanted in the patient for reversing the restriction device 8. When the switch is operated by polarized energy the wireless remote control of the external energy-transmission device 1004 transmit a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the restriction device 8.

FIG. 17 shows an embodiment of the invention identical to that of FIG. 15, except that an operation device 1007 implanted in the patient for operating the restriction device 8 is provided between the implanted energy-transforming device 1002 and the restriction device 8. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 18 shows an embodiment of the invention identical to that of FIG. 15, except that it also comprises an operation device in the form of an assembly 1008 including a motor/pump unit 1009 and a fluid reservoir 1010 is implanted in the patient. In this case the restriction device 8 is hydraulically operated, i.e. hydraulic fluid is pumped by the motor/pump unit 1009 from the fluid reservoir 1010 through a conduit 1011 to the restriction device 8 to operate the restriction device 8, and hydraulic fluid is pumped by the motor/pump unit 1009 back from the restriction device 8 to the fluid reservoir 1010 to return the restriction device 8 to a starting position. The implanted energy-transforming device 1002 transforms wireless energy into a current, for example a polarized current, for powering the motor/pump unit 1009 via an electric power supply line 1012.

Instead of a hydraulically operated restriction device 8, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 19:
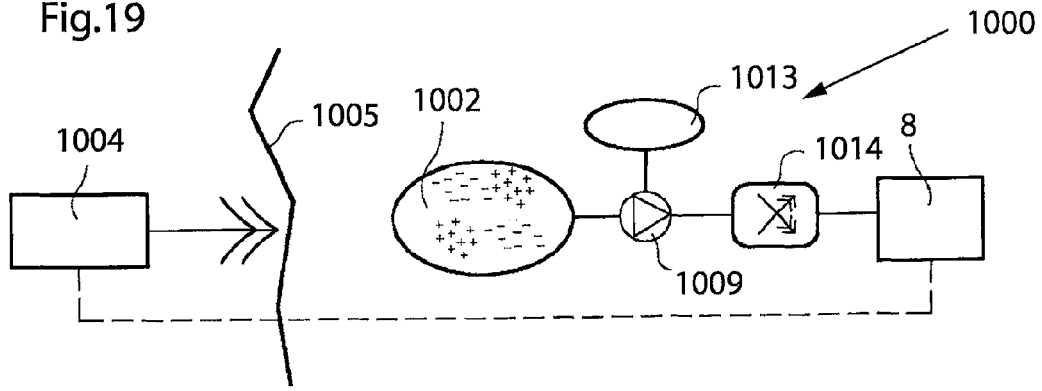

FIG. 19 shows an embodiment of the invention comprising the external energy-transmission device 1004 with its wireless remote control, the restriction device 8, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the restriction device 8. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the restriction device 8 to operate the restriction device 8, and another opposite direction in which the fluid is pumped by the motor/pump unit 1009 back from the restriction device 8 to the hydraulic fluid reservoir 1013 to return the restriction device 8 to a starting position.

Figure 20:
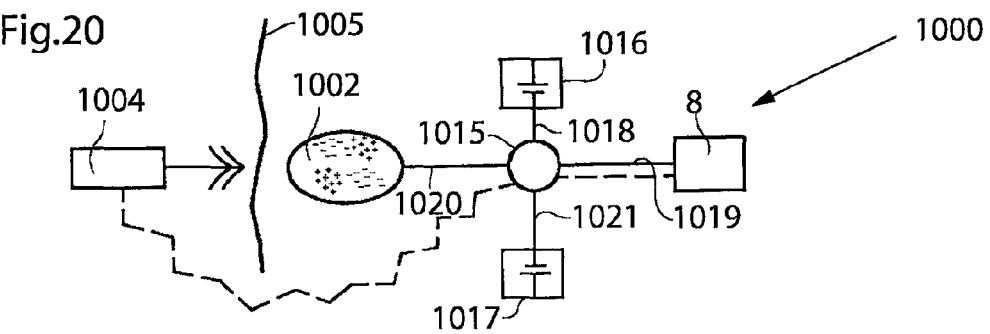

FIG. 20 shows an embodiment of the invention comprising the external energy-transmission device 1004 with its wireless remote control, the restriction device 8, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the restriction device 8. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the restriction device 8.

The internal control unit is preferably programmable from outside the patient's body. In a preferred embodiment, the internal control unit is programmed to regulate the restriction device 8 according to a pre-programmed time-schedule or to input from any sensor sensing any possible physical parameter of the patient or any functional parameter of the system.

In accordance with an alternative, the capacitor 1017 in the embodiment of FIG. 20, 10 may be omitted. In accordance with another alternative, the accumulator 1016 in this embodiment may be omitted.

Figure 21:
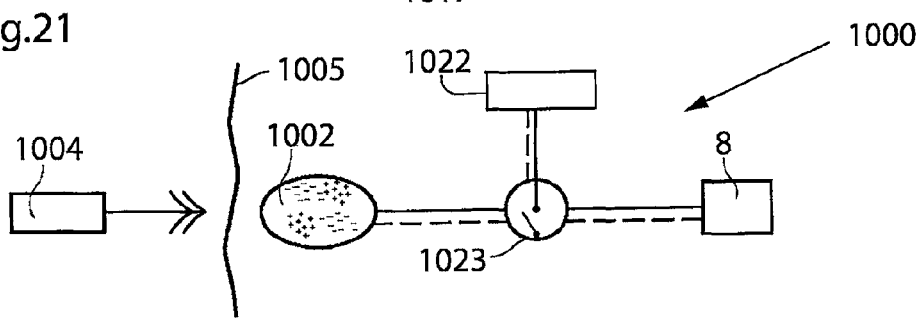

FIG. 21 shows an embodiment of the invention identical to that of FIG. 15, except that a battery 1022 for supplying energy for the operation of the restriction device 8 and an electric switch 1023 for switching the operation of the restriction device 8 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the restriction device 8.

Figure 22:
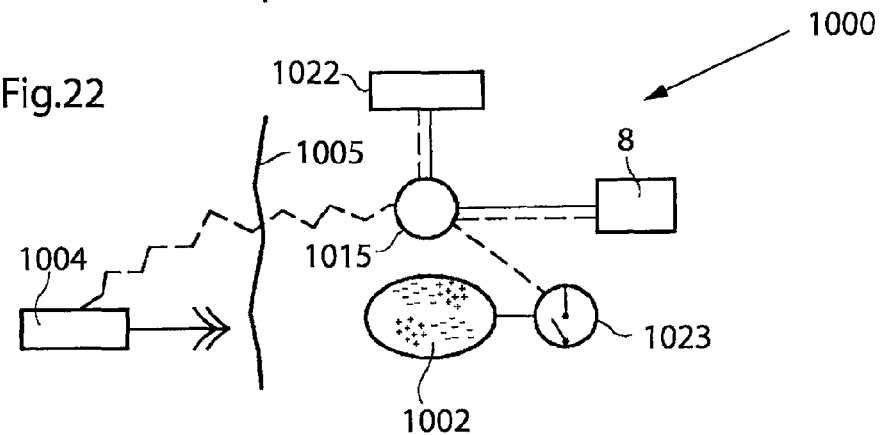

FIG. 22 shows an embodiment of the invention identical to that of FIG. 21, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the restriction device 8.

Figure 23:
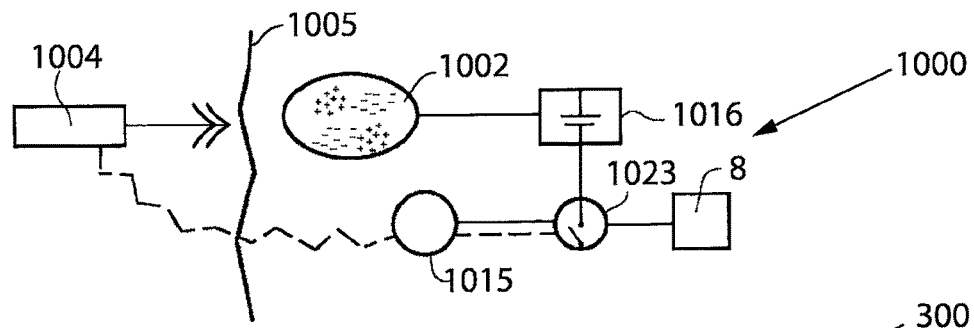

FIG. 23 shows an embodiment of the invention identical to that of FIG. 22, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the restriction device 8. The accumulator may be combined with or replaced by a capacitor.

Figure 24:
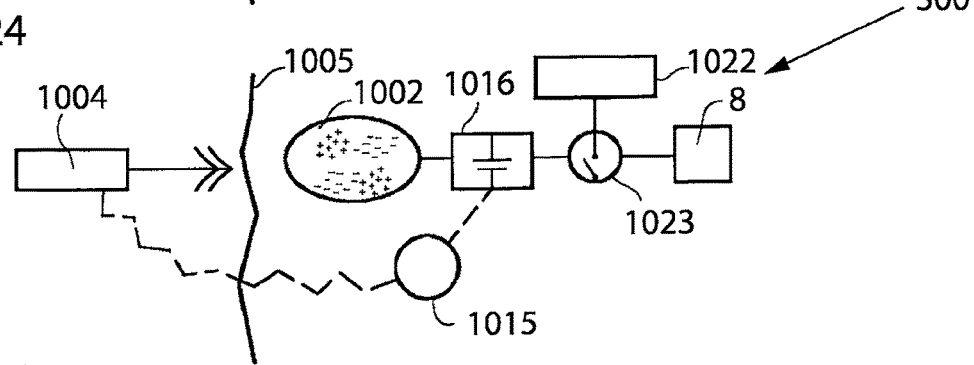

FIG. 24 shows an embodiment of the invention identical to that of FIG. 23, except that a battery 1022 also is implanted in the patient and the implanted component are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the restriction device 8.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the restriction device 8.

It should be understood that the switch 1023 and all other switches in this application should be interpreted in it broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 25:
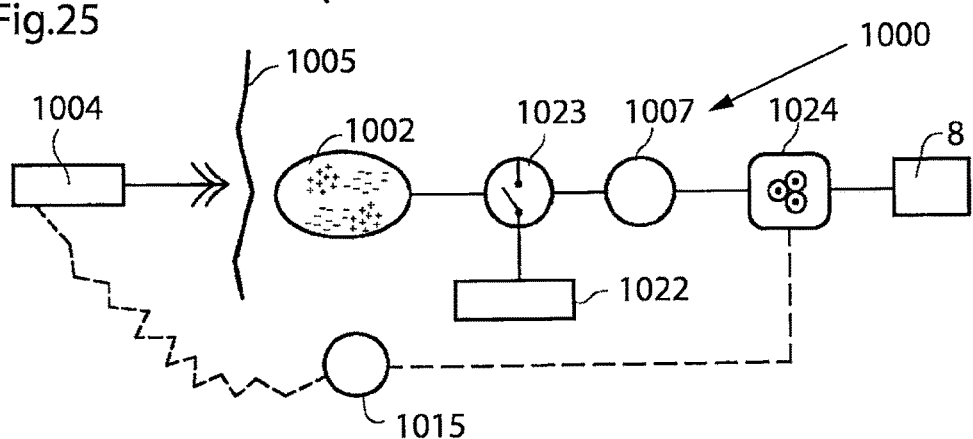

FIG. 25 shows an embodiment of the invention identical to that of FIG. 21, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the restriction device 8 (mechanically operated). Even simpler is to switch the direction of the motor electronically. The gear box interpreted in its broadest embodiment may stand for a servo arrangement saving force for the operation device in favour of longer stroke to act.

Figure 26:
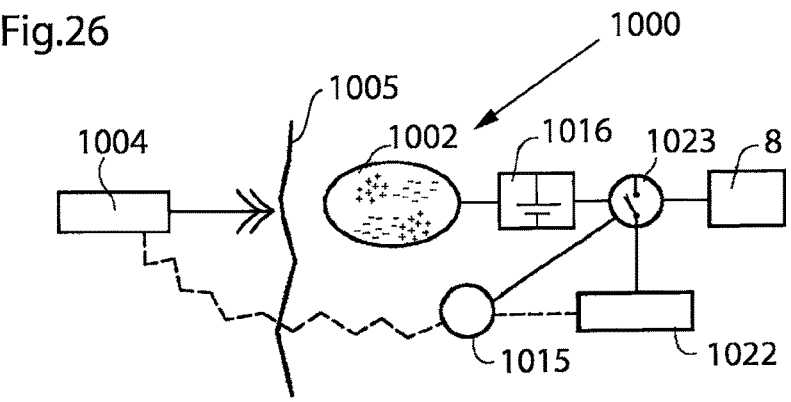

FIG. 26 shows an embodiment of the invention identical to that of FIG. 25 except that the implanted component are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the restriction device 8.

Figure 27:
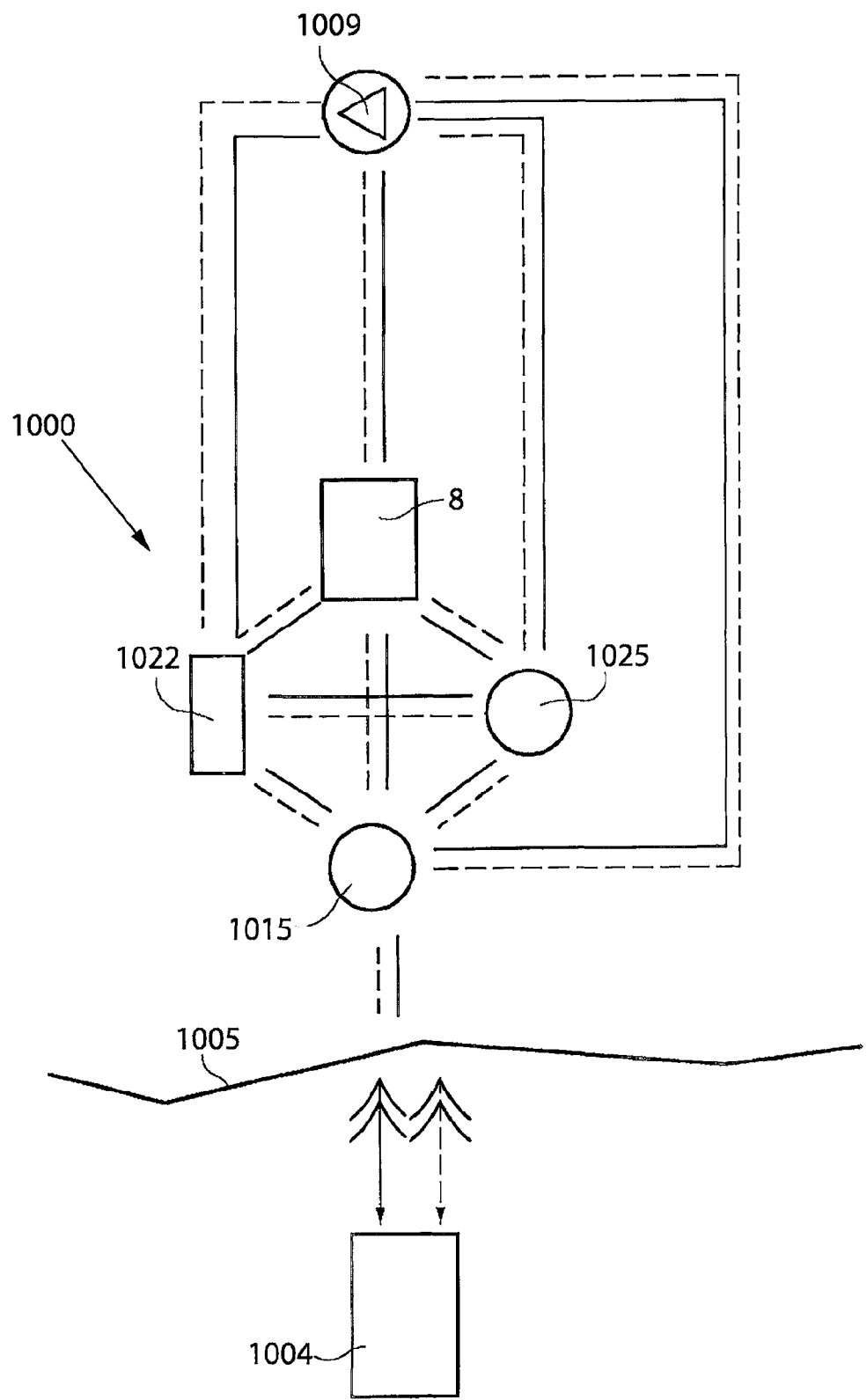

FIG. 27 schematically shows conceivable combinations of implanted component of the restriction device 8 for achieving various communication options. Basically, there are the restriction device 8, the internal control unit 1015, motor or pump unit 1009, and the external energy-transmission device 1004 including the external wireless remote control. As already described above the wireless remote control transmit a control signal which is received by the internal control unit 1015, which in turn controls the various implanted component of the restriction device 8.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the restriction device 8 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the restriction device 8 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feedback information related to said charging process is sent and the energy supply is changed accordingly.

Figure 28:
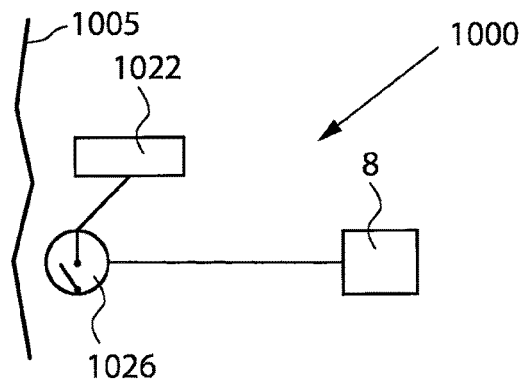

FIG. 28 shows an alternative embodiment wherein the restriction device 8 is regulated from outside the patient's body. The system 1000 comprises a battery 1022 connected to the restriction device 8 via a subcutaneous electric switch 1026. Thus, the regulation of the restriction device 8 is performed non-invasively by manually pressing the subcutaneous switch, whereby the operation of the restriction device 8 is switched on and off. It will be appreciated that the shown embodiment is a simplification and that additional component, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 29:
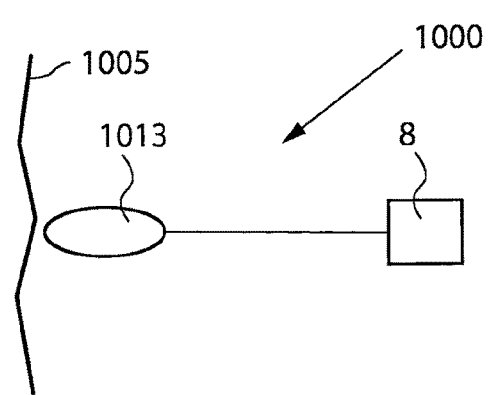

FIG. 29 shows an alternative embodiment, wherein the system 1000 comprises a hydraulic fluid reservoir 1013 hydraulically connected to the restriction device 8. Non-invasive regulation is performed by manually pressing the hydraulic reservoir connected to the restriction device 8. Alternatively, the hydraulic fluid reservoir 1013 is adapted to work with an injection port for the injection of hydraulic fluid, preferably for calibration of hydraulic fluid.

The system may include an external data communicator and an implantable internal data communicator communicating with the external data communicator. The internal communicator feeds data related to the restriction device 8 or the patient to the external data communicator and/or the external data communicator feeds data to the internal data communicator.

Figure 30:
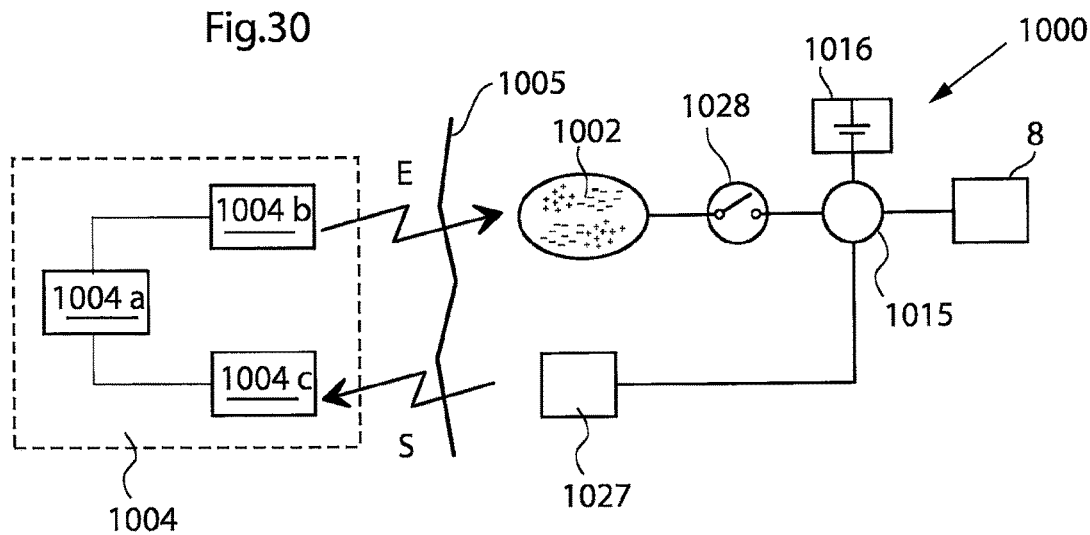
FIG. 30 is a schematic block diagram illustrating an arrangement for supplying an accurate amount of energy used for the operation of the restriction device and component connected thereto shown in FIG. 14.

FIG. 30 schematically illustrates an arrangement of the system that is capable of sending information from inside the patient's body to the outside thereof to give feedback information related to at least one functional parameter of the restriction device 8 or system, or related to a physical parameter of the patient, in order to supply an accurate amount of energy to an implanted internal energy receiver 1002 connected to implanted energy consuming component of the restriction device 8. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming component of the restriction device 8 via a switch 1026. An energy balance is determined between the energy received by the internal energy receiver 1002 and the energy used for the restriction device 8, and the transmission of wireless energy is then controlled based on the determined energy balance. The energy balance thus provides an accurate indication of the correct amount of energy needed, which is sufficient to operate the restriction device 8 properly, but without causing undue temperature rise.

In FIG. 30 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the restriction device 8, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted component of the restriction device 8. The term "energy used" is then understood to include also energy stored by implanted component of the restriction device 8. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the restriction device 8. The internal control unit 1015 may thus be arranged to receive various measurements obtained by suitable sensors or the like, not shown, measuring certain characteristics of the restriction device 8, somehow reflecting the required amount of energy needed for proper operation of the restriction device 8. Moreover, the current condition of the patient may also be detected by means of suitable measuring devices or sensors, in order to provide parameters reflecting the patient's condition. Hence, such characteristics and/or parameters may be related to the current state of the restriction device 8, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the restriction device 8. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the restriction device 8, and also to avoid excessive heating, it is clearly understood that the battery should be charged optimally by receiving a correct amount of energy from the implanted energy-transforming device 1002, i.e. not too lithe or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the restriction device 8, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004b. The energy balance and the currently required amount of energy can then be determined by the external control unit 1004b based on those sensor measurements.

Hence, the present solution according to the arrangement of FIG. 30 employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the restriction device 8. Me restriction device 8 may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the restriction device 8.

The internal signal transmitter 1027 and the external signal receiver 1004*c* may be implemented as separate unit using suitable signal transfer means, such as radio, IR (Infrared) or ultrasonic signals. Alternatively, the internal signal transmitter 1027 and the external signal receiver 1004*c* may be integrated in the implanted energy-transforming device 1002 and the external energy source 1004*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmit wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 30, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 30 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004*c*. Alternatively, the energy balance can be determined by the external control unit 1004*b* instead depending on the implementation, as mentioned above. In that case, the control signal may carry measurement results from various sensors. The amount of energy emitted from the external energy source 1004*a* can then be regulated by the external control unit 1004*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004*a*, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmit wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 31:
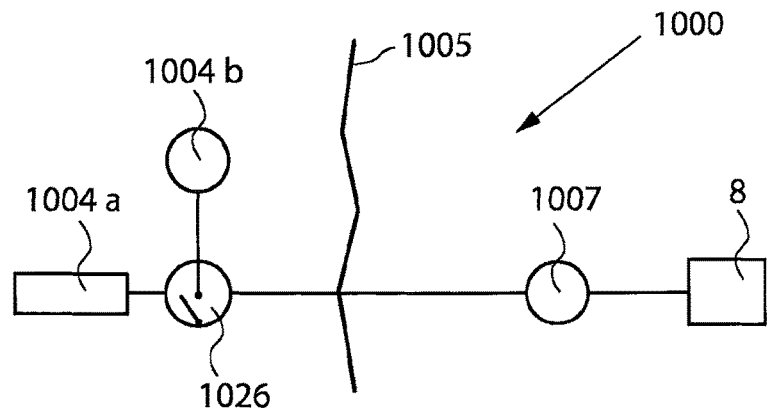
FIG. 31 schematically shows an embodiment of the system, in which the restriction device is operated with wire-bound energy.

With reference to FIG. 31, although wireless transfer of energy for operating the restriction device 8 has been described above to enable non-invasive operation, it will be appreciated that the restriction device 8 can be operated with wire bound energy as well. Such an example is shown in FIG. 31, wherein an external switch 1026 is interconnected between the external energy source 1004*a* and an operation device, such as an electric motor 1007 operating the restriction device 8. An external control unit 1004*b* controls the operation of the external switch 1026 to effect proper operation of the restriction device 8.

Figure 32:
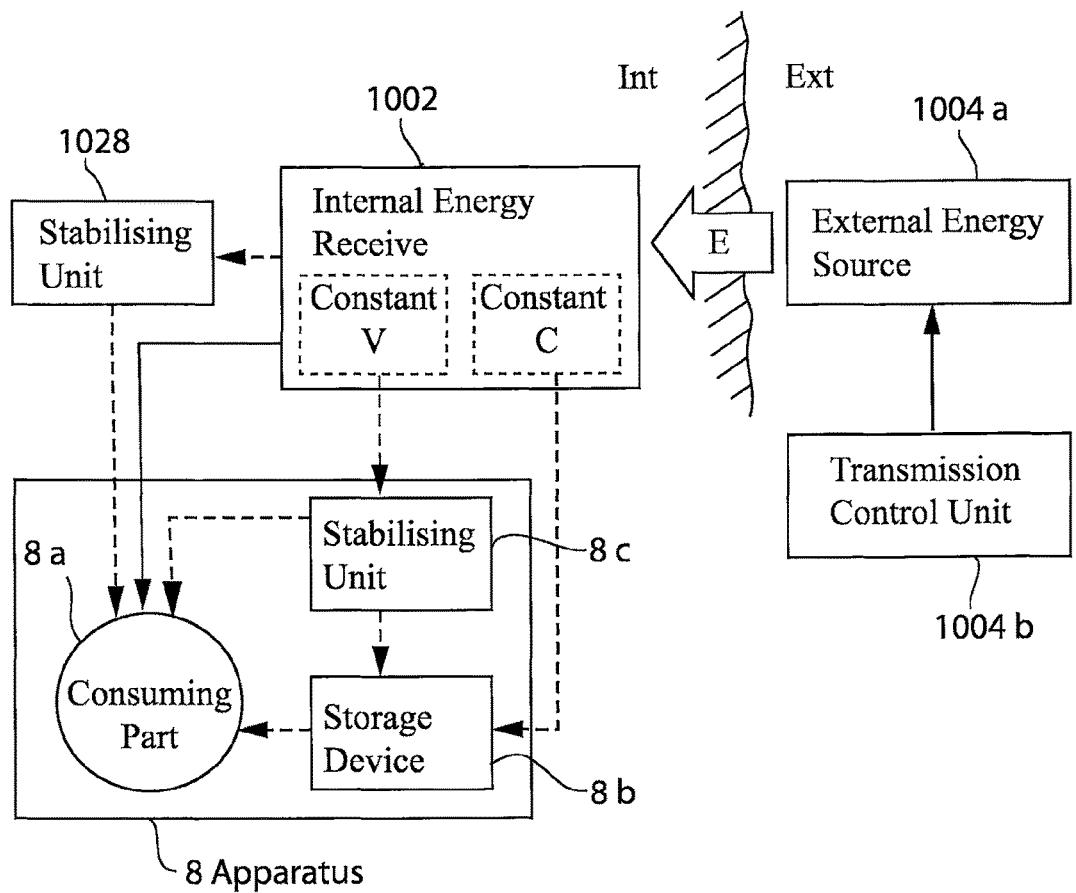
FIG. 32 is a more detailed block diagram of an arrangement for controlling the transmission of wireless energy used for the operation of the restriction device shown in FIG. 14.

FIG. 32 illustrates different embodiments for how received energy can be supplied to and used by the restriction device 8. Similar to the example of FIG. 30, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the restriction device 8. The internal energy receiver 1002 may further comprise a constant current circuit, indicated as a dashed box "constant C" in the figure, for supplying energy at constant current to the restriction device 8.

The restriction device 8 comprises an energy consuming part 8*a*, which may be a motor, pump, restriction device, or any other medical appliance that requires energy for its electrical operation. The restriction device 8 may further comprise an energy storage device 8*b* for storing energy supplied from the internal energy receiver 1002. Thus, the supplied energy may be directly consumed by the energy consuming part 8*a*, or stored by the energy storage device 8*b*, or the supplied energy may be partly consumed and partly stored. The restriction device 8 may further comprise an energy stabilizing unit 8*c* for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the restriction device 8, before being consumed and/or stored by the restriction device 8. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 30 and FIG. 32 illustrate some possible but non-limiting implementation options regarding how the various shown functional components and elements can be arranged and connected to each other. However, the skilled person will readily appreciate that many variations and modifications can be made within the scope of the present invention.

Figure 33:
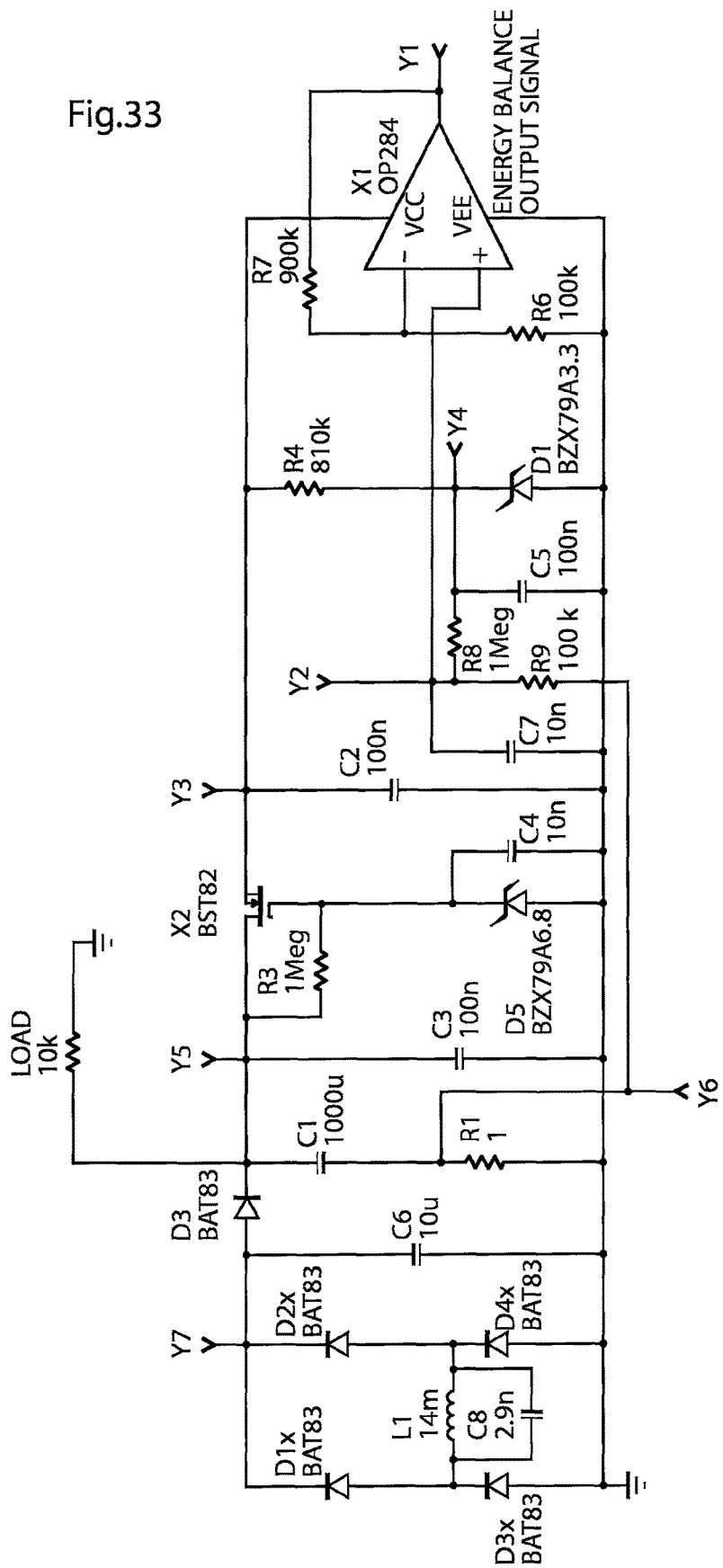
FIG. 33 is a circuit for the arrangement shown in FIG. 32, according to a possible implementation example.

FIG. 33 schematically shows an energy balance measuring circuit of one of the proposed designs of the system for controlling transmission of wireless energy, or energy balance control system. The circuit has an output signal centred on 2.5V and proportionally related to the energy imbalance. The derivative of this signal shows if the value goes up and down and how fast such a change takes place. If the amount of received energy is lower than the energy used by implanted component of the restriction device 8, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analogue system that uses comparators comparing the energy balance level with certain maximum and minimum thresholds sending information to external energy-transmission device if the balance drifts out of the max/min window.

The schematic FIG. 33 shows a circuit implementation for a system that transfers energy to the implanted energy components of the restriction device 8 of the present invention from outside of the patient's body using inductive energy transfer. An inductive energy transfer system typically uses an external transmitting coil and an internal receiving coil. The receiving coil, L1, is included in the schematic FIG. 33; the transmitting part of the system are excluded.

The implementation of the general concept of energy balance and the way the information is transmitted to the external energy transmitter can of course be implemented in numerous different ways. The schematic FIG. 33 and the above described method of evaluating and transmitting the information should only be regarded as examples of how to implement the control system.

Circuit Details

In FIG. 33 the symbols Y1, Y2, Y3 and so on symbolize test points within the circuit. The component in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 16 could be incorporated in any of the embodiments of FIGS. 19-25, the hydraulic valve shilling device 1014 of FIG. 19 could be incorporated in the embodiment of FIG. 18, and the gear box 1024 could be incorporated in the embodiment of FIG. 17. Please observe that the switch simply could mean any electronic circuit or component.

The embodiments described in connection with FIGS. 30, 32 and 33 identify a method and a system for controlling transmission of wireless energy to implanted energy consuming component of an electrically operable restriction device 8. Such a method and system will be defined in general terms in the following.

A method is thus provided for controlling transmission of wireless energy supplied to implanted energy consuming component of a restriction device 8 as described above. The wireless energy E is transmitted from an external energy source located outside the patient and is received by an internal energy receiver located inside the patient, the internal energy receiver being connected to the implanted energy consuming components of the restriction device 8 for directly or indirectly supplying received energy thereto. An energy balance is determined between the energy received by the internal energy receiver and the energy used for the restriction device 8. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. Me total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an restriction device 8 as described above is thus also provided for controlling transmission of wireless energy supplied to implanted energy consuming component of the restriction device 8. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the restriction device 8 for directly or indirectly supplying received energy thereto. The system further comprises a determination device adapted to determine an energy balance between the energy received by the internal energy receiver and the energy used for the implantable energy consuming component of the restriction device 8, wherein the control device controls the transmission of wireless energy from the external energy-transmission device, based on the energy balance determined by the determination device.

In one embodiment at least one battery may be a part of or replace the energy-transforming device 1002 to supply energy to the restriction device 8 over a power supply line. In one embodiment the battery is not rechargeable. In an alternative embodiment the battery is rechargeable. The battery supply may of course be placed both remote to and incorporated in the device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming component of the restriction device 8, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the restriction device 8 is consumed to operate the restriction device 8, and/or stored in at least one energy storage device of the restriction device 8.

Where electrical and/or physical parameters of the restriction device 8 and/or physical parameters of the patient are determined, the energy-transmission device transmit the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 34-37 show in more detail block diagrams of four different ways of hydraulically or pneumatically powering the implanted restriction device 8 according to the invention.

Figure 34:
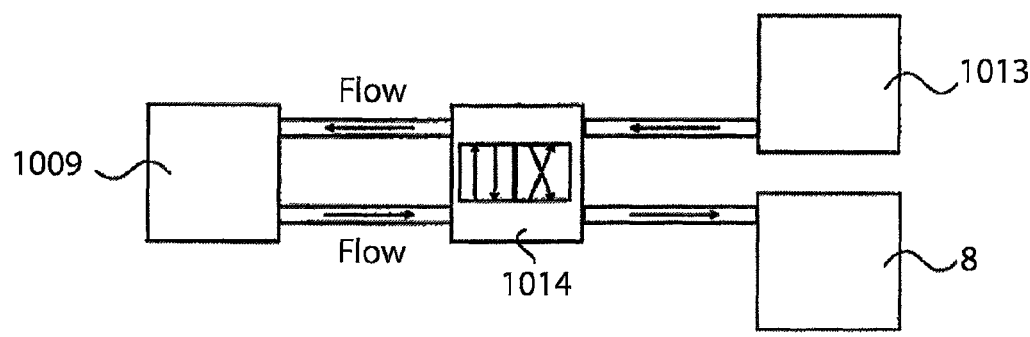
FIGS. 34-40 show various ways of arranging hydraulic or pneumatic powering of a restriction device implanted in a patient.

FIG. 34 shows a system as described above, but hydraulically regulated. The system comprises an implanted restriction device 8 and further a separate regulation reservoir 1013, a one way pump 1009 and an alternate valve 1014.

Figure 35:
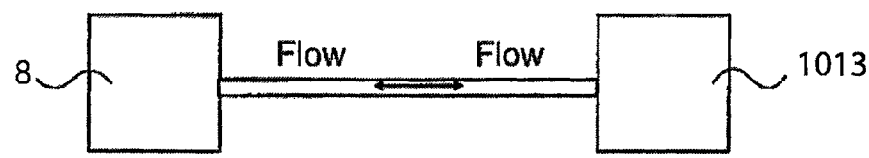

FIG. 35 shows the restriction device 8 and a fluid reservoir 1013. By moving the wall of the regulation reservoir or changing the size of the same in any other different way, the adjustment of the restriction device 8 may be performed without any valve, just free passage of fluid any time by moving the reservoir wall.

Figure 36:
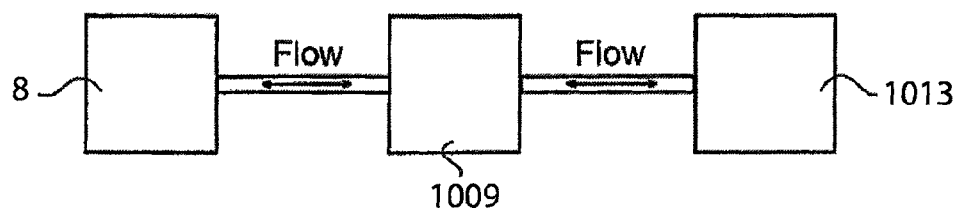

FIG. 36 shows the restriction device 8, a two way pump 1009 and the regulation reservoir 1013.

Figure 37:
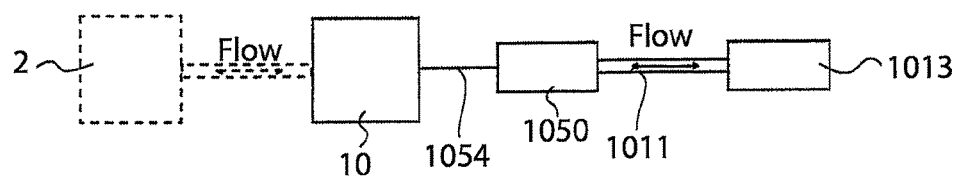

FIG. 37 shows a block diagram of a reversed servo system with a first closed system controlling a second closed system. The servo system comprises a regulation reservoir 1013 and a servo reservoir 1050. The servo reservoir 1050 mechanically controls an implanted restriction device 8 via a mechanical interconnection 1054. The restriction device 8 has an expandable/contactable cavity. This cavity is preferably expanded or contracted by supplying hydraulic fluid from the larger adjustable reservoir 1052 in fluid connection with the restriction device 8. Alternatively, the cavity contains compressible gas, which can be compressed and expanded under the control of the servo reservoir 1050.

The servo reservoir 1050 can also be part of the restriction device 8 itself.

Figure 38A:
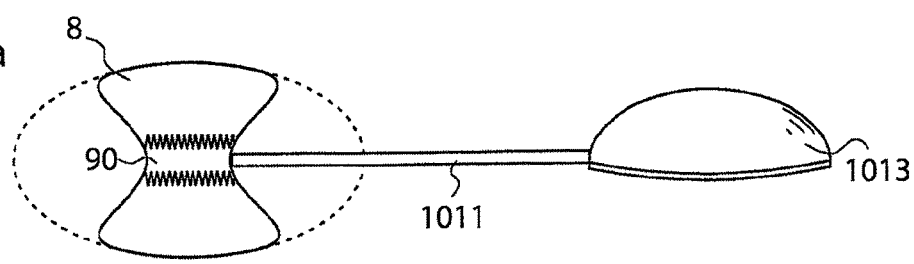
Figure 38B:
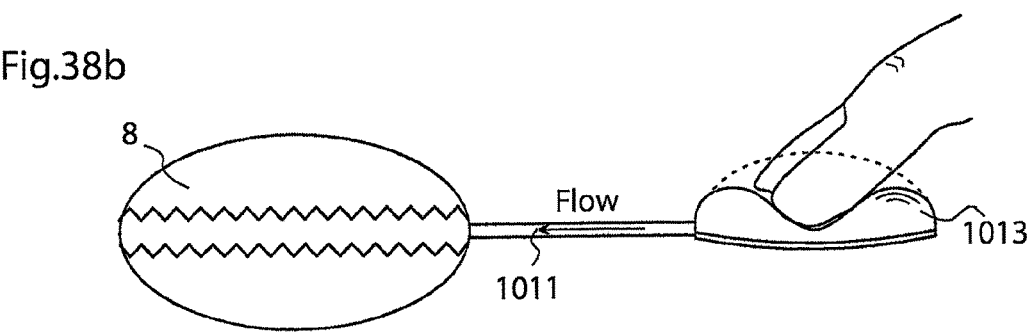
Figure 38C:
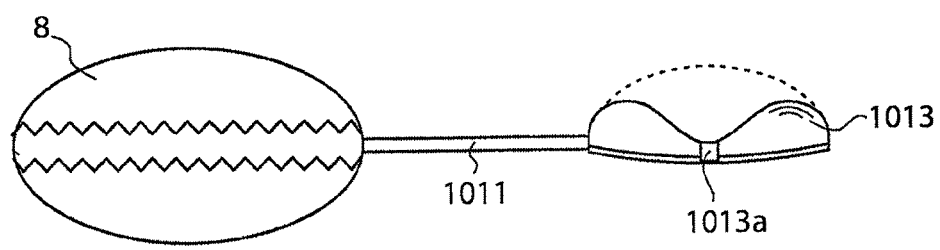
Figure 39:
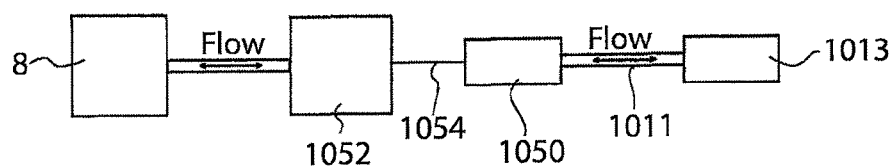

In one embodiment, the regulation reservoir is placed subcutaneous under the patient's skin and is operated by pushing the outer surface thereof by means of a finger. This system is illustrated in FIGS. 38*a-c*. In FIG. 38*a*, a flexible subcutaneous regulation reservoir 1013 is shown connected to a bulge shaped servo reservoir 1050 by means of a conduit 1011. This bellow shaped servo reservoir 1050 is comprised in a flexible restriction device 8. In the state shown in FIG. 38*a*, the servo reservoir 1050 contains a minimum of fluid and most fluid is found in the regulation reservoir 1013. Due to the mechanical interconnection between the servo reservoir 1050 and the restriction device 8, the outer shape of the restriction device 8 is contracted, i.e., it occupies less than it maximum volume. This maximum volume is shown with dashed lines in the figure.

FIG. 38*b* shows a state wherein a user, such as the patient in with the restriction device 8 is implanted, presses the regulation reservoir 1013 so that fluid contained therein is brought to flow through the conduit 1011 and into the servo reservoir 1050, which, thanks to its bellow shape, expands longitudinally. This expansion in turn expands the restriction device 8 so that it occupies its maximum volume, thereby stretching the stomach wall (not shown), which it contact.

The regulation reservoir 1013 is preferably provided with means 1013*a* for keeping its shape after compression. This means, which is schematically shown in the figure, will thus keep the restriction device 8 in a stretched position also when the user releases the regulation reservoir. In this way, the regulation reservoir essentially operates as an on/off switch for the system.

An alternative embodiment of hydraulic or pneumatic operation will now be described with reference to FIGS. 39 and 40*a-c*. The block diagram shown in FIG. 39 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted restriction device 8 having an expandable/contactable cavity is in turn controlled by the larger adjustable reservoir 1052 by supply of hydraulic fluid from the larger adjustable reservoir 1052 in fluid connection with the restriction device 8.

Figure 40A:
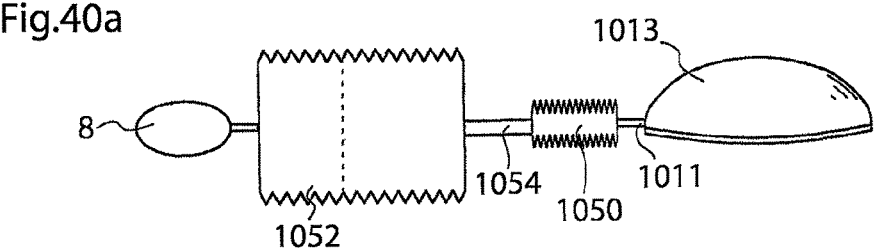
Figure 40B:
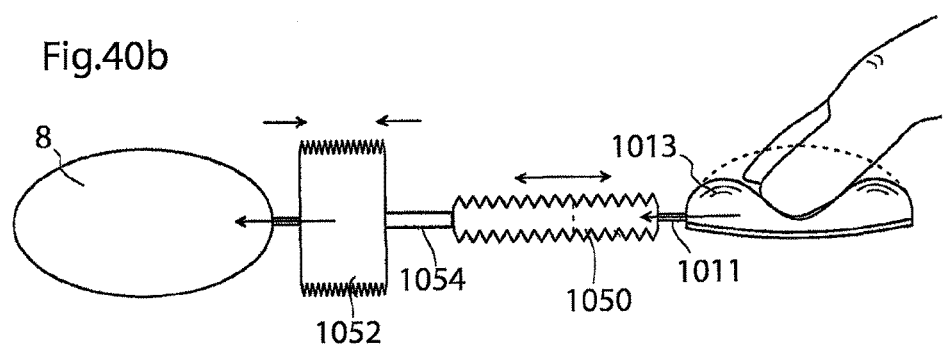
Figure 40C:
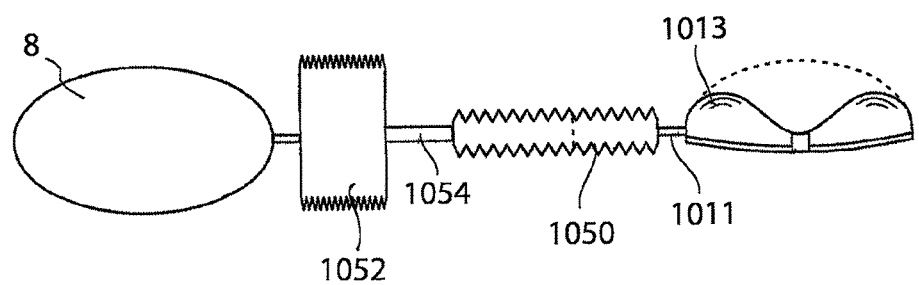

An example of this embodiment will now be described with reference to FIG. 40*a-c*. like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 40*a*, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the restriction device 8. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the restriction device 8. In other words, in this reversed servo, a small volume in the regulation reservoir is compressed with a higher force and this creates a movement of a larger total area with less force per area unit.

Like in the previous embodiment described above with reference to FIGS. 38a-c, the regulation reservoir 1013 is preferably provided with means 1013a for keeping its shape after compression. This means, which is schematically shown in the figure, will thus keep the restriction device 8 in a stretched position also when the user releases the regulation reservoir. In this way, the regulation reservoir essentially operates as an on/off switch for the system.

Although the different part described above have specific placements on the drawings it should be understood that these placements might vary, depending on the application.

In all of the embodiments above it is conceivable that the conduit is excluded and that the channel or channels are in direct connection with the reservoir or the injection port. Please note that any embodiment or part of embodiment as well as any method or part of method could be combined in any way. All examples herein should be seen as part of the general description and therefore possible to combine in any way in general terms.

The various aforementioned features of the method may be combined in any way if such combination is not clearly contradictory. Again, individual features of the various embodiments may be combined or exchanged unless such combination or exchange is clearly contradictory to the overall function of the method.

The invention claimed is:

1. A surgical instrument for accessing an opening in the vaginal wall of a patient, the instrument comprising:
   an elongated main part,
   an elongated member having a proximal end fixed to a distal end of the elongated main part by means of a first adjustable joint having a pivotal axis, for adjusting a first angle between the main part of the instrument and the elongated member between 0 and 180 degrees, wherein
   the elongated main part and the elongated member lie in a first plane extending perpendicularly to the pivotal axis;
   a flexible tip attached to a distal end of the elongated member and exhibiting a conformation which is reversibly changeable from an essentially straight conformation to a loop or hook conformation, wherein the flexible tip, when in the loop or hook conformation, defines an opening with an axial hole going there through, and wherein a second plane extends perpendicularly to the axial hole through said loop or hook, so that the flexible tip, in its loop or hook conformation, lies in the second plane, and
   wherein
   the elongated member has a length allowing the elongated member to be placed such that it extends through the opening in the vaginal wall when the elongated main part is arranged in the vagina of the patient, the length thereby allowing the flexible tip to be placed in a position, wherein it at least partly encloses the rectum or colon of the patient,
   the flexible tip comprises a dissector and an attachment structure adapted to attach to an implantable medical device,
   the first adjustable joint and the elongated member are adjustable independently from the change of the conformation of the flexible tip, and
   the orientation of the first plane is different from the orientation of the second plane.

2. The surgical instrument according to claim 1, wherein the elongated member can be turned around its own axis so that the plane of the loop or hook is continuously adjustable.

3. The surgical instrument according to claim 1, wherein the attachment structure comprises a quick coupling.

4. The surgical instrument according to claim 1, wherein the attachment structure comprises a pincer.

5. The surgical instrument according to claim 1, wherein the instrument comprises a viewing scope.

6. The surgical instrument according to claim 1, wherein the dissector is a soft tissue dissector.

7. The surgical instrument according to claim 1, wherein the first angle is between 0 and less than 180 degrees.

8. The surgical instrument according to claim 1, wherein the first angle is between 60 and 150 degrees.

9. The surgical instrument according to claim 1 wherein the first angle is in an interval between 90 and 180 degrees.

10. The surgical instrument according to claim 9, wherein the first angle is adapted to be variable within said interval.

11. The surgical instrument according to claim 1, comprising an additional joint placed distal to the first adjustable joint, towards the flexible tip, dividing the elongated member into two parts, wherein the additional joint is adapted to create a second angle between said two parts of the elongated member, wherein the second angle is adapted to be adjustable between 0 and less than 180 degrees.

12. The surgical instrument according to claim 11, wherein the second angle is adapted to be adjustable to between 90 and 180 degrees.

13. The surgical instrument according to claim 11, wherein the second angle is adapted to be adjustable to between 90 and 150 degrees.

14. The surgical instrument according to claim 11, wherein a distal part of the elongated member, distal to the additional joint, can be turned around its own axis so that the plane of the loop is continuously adjustable.

15. The surgical instrument according to claim 1, wherein the main part of the instrument is extendable.

16. The surgical instrument according to claim 1, wherein the main part of the instrument is continuously extendable.

17. The surgical instrument according to claim 1, wherein the change of conformation of the loop is achieved by wires that run inside the flexible tip.

18. The surgical instrument according to claim 1, wherein the first adjustable joint is adapted to adjust the first angle between the main part of the instrument and the elongated member, independently of the conformation of the flexible tip.

19. The surgical instrument according to claim 1, further comprising a control unit adapted to independently control any parameter from the group selected from: the change of conformation of the flexible tip, the attachment structure, the first angle, the second angle, turning of the elongated member around its own axis, turning of the elongated member's two parts around their own axis independently from each other and extension of the main part of the instrument.

20. The surgical instrument according to claim 19, wherein the control unit is integrated into a handle of the instrument.

\* \* \* \* \*